US007829313B2

(12) United States Patent
Alexandre et al.

(10) Patent No.: US 7,829,313 B2
(45) Date of Patent: Nov. 9, 2010

(54) IDENTIFICATION AND QUANTIFICATION OF A PLURALITY OF BIOLOGICAL (MICRO)ORGANISMS OR THEIR COMPONENTS

(75) Inventors: Isabelle Alexandre, Haltinne (BE); Sylvain Margaine, Namur (BE); Dieter Husar, Hamburg (DE); Nathalie Zammatteo, Gelbressee (BE); Heinz Koehn, Hamburg (DE); José Remacle, Malonne (BE)

(73) Assignee: Eppendorf Array Technologies, Namur (BE)

( * ) Notice: Subject to any disclaimer, the term of this patent is extended or adjusted under 35 U.S.C. 154(b) by 386 days.

(21) Appl. No.: 11/441,393

(22) Filed: May 24, 2006

(65) Prior Publication Data

US 2007/0099204 A1    May 3, 2007

Related U.S. Application Data

(63) Continuation-in-part of application No. 11/436,383, filed on May 17, 2006, which is a continuation-in-part of application No. 10/056,229, filed on Jan. 23, 2002, now Pat. No. 7,202,026, which is a continuation-in-part of application No. 09/817,014, filed on Mar. 23, 2001, now Pat. No. 7,205,104, application No. 11/441, 393, which is a continuation-in-part of application No. PCT/EP2005/012383, filed on Nov. 18, 2005.

(51) Int. Cl.
*C12P 19/34* (2006.01)
*C12M 1/00* (2006.01)

(52) U.S. Cl. .................... 435/91.2; 435/283.1
(58) Field of Classification Search .............. 435/6, 435/91.2
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,195 A | 7/1987 | Mullis et al. |
| 4,683,202 A | 7/1987 | Mullis et al. |
| 5,011,769 A | 4/1991 | Duck et al. |
| 5,143,854 A | 9/1992 | Pirrung et al. |
| 5,312,527 A | 5/1994 | Mikkelsen et al. |
| 5,445,934 A | 8/1995 | Fodor et al. |
| 5,451,512 A | 9/1995 | Apple et al. |
| 5,510,270 A | 4/1996 | Fodor et al. |
| 5,552,270 A | 9/1996 | Khrapko et al. |
| 5,587,307 A | 12/1996 | Alborn, Jr. et al. |
| 5,633,724 A | 5/1997 | King et al. |
| 5,683,872 A | 11/1997 | Rudert et al. |
| 5,723,591 A | 3/1998 | Livak et al. |
| 5,736,257 A | 4/1998 | Conrad et al. |
| 5,744,305 A | 4/1998 | Fodor et al. |
| 5,753,439 A | 5/1998 | Smith et al. |
| 5,770,721 A | 6/1998 | Ershov et al. |
| 5,800,992 A | 9/1998 | Fodor et al. |
| 5,807,522 A | 9/1998 | Brown et al. |
| 5,821,060 A | 10/1998 | Arlinghaus et al. |
| 6,207,648 B1 | 3/2001 | Waxman et al. |
| 6,228,575 B1 | 5/2001 | Gingeras et al. |
| 6,232,114 B1 * | 5/2001 | Coassin et al. ............ 435/288.4 |
| 6,255,059 B1 | 7/2001 | Klein et al. |
| 6,270,965 B1 | 8/2001 | Kleiber et al. |
| 6,306,643 B1 | 10/2001 | Gentalen et al. |
| 6,331,441 B1 | 12/2001 | Balch et al. |
| 6,346,413 B1 | 2/2002 | Fodor et al. |
| 6,416,951 B1 | 7/2002 | Schmidt et al. |
| 6,488,932 B1 | 12/2002 | Boon et al. |
| 6,503,711 B1 | 1/2003 | Krull et al. |
| 6,541,617 B1 | 4/2003 | Bamdad et al. |
| 6,589,740 B2 | 7/2003 | Nakao et al. |
| 2002/0102578 A1 | 8/2002 | Dickinson et al. |
| 2002/0177135 A1* | 11/2002 | Doung et al. ................ 435/6 |
| 2003/0198943 A1 | 10/2003 | Remacle et al. |
| 2005/0106126 A1 | 5/2005 | Whitlock |
| 2006/0003308 A1 | 1/2006 | Kulisch |
| 2006/0088844 A1 | 4/2006 | Xu |
| 2006/0106354 A1 | 5/2006 | Vantroostenberghe |

FOREIGN PATENT DOCUMENTS

| DE | 199 49 735 | 5/2001 |
| EP | 0 511 559 | 11/1992 |
| EP | 0 476 014 | 8/1994 |
| EP | 0 535 242 | 9/1997 |
| EP | 0 721 016 | 11/1999 |

(Continued)

OTHER PUBLICATIONS

Ahern et al. The Scientist, vol. 9, n0. 15, pp. 1-5, Jul. 1995.*

(Continued)

*Primary Examiner*—Gary Benzion
*Assistant Examiner*—Cynthia B Wilder
(74) *Attorney, Agent, or Firm*—Howrey LLP

(57) ABSTRACT

Disclosed is a system and method conducting real-time PCR. Capture molecules of a specific design are immobilized on a solid support, and contacted with amplicons produced in one or more PCR cycles. Detection of amplicons may take place during or between the PCR cycles while the solid support is in fluidic contact with the PCR solution. In an alternate embodiment detection of the amplicons takes place when the solid support is not in fluidic contact with the PCR solution. The method is suitable for the simultaneous detection and quantification of closely homologous target molecules.

14 Claims, 14 Drawing Sheets

FOREIGN PATENT DOCUMENTS

| | | |
|---|---|---|
| EP | 0 785 280 | 4/2003 |
| EP | 1 659 183 A | 5/2006 |
| GB | 2 318 791 | 6/1998 |
| WO | WO 89/11548 | 11/1989 |
| WO | WO 94/05695 | 3/1994 |
| WO | WO 95/11995 | 5/1995 |
| WO | WO 96/31622 | 10/1996 |
| WO | WO 97/10364 | 3/1997 |
| WO | WO 97/10365 | 3/1997 |
| WO | WO 97/27317 | 7/1997 |
| WO | WO 97/27329 | 7/1997 |
| WO | WO 97/29212 | 8/1997 |
| WO | WO 97/31256 | 8/1997 |
| WO | WO 98/11253 | 3/1998 |
| WO | WO 98/28438 | 7/1998 |
| WO | WO 98/28444 | 7/1998 |
| WO | WO 99/16780 | 4/1999 |
| WO | WO 99/20789 | 4/1999 |
| WO | WO 99/32660 | 7/1999 |
| WO | WO 99/35499 | 7/1999 |
| WO | WO 00/12675 | 3/2000 |
| WO | WO 00/72018 | 11/2000 |
| WO | WO 01/27327 | 4/2001 |
| WO | WO 01/27327 A2 | 4/2001 |
| WO | WO 01/31055 | 5/2001 |
| WO | WO 01/77372 | 10/2001 |
| WO | WO 02/18288 | 3/2002 |
| WO | WO 03/052421 | 6/2003 |
| WO | WO 2004/101733 A | 11/2004 |
| WO | WO 2006/053769 A | 5/2006 |
| WO | WO 2006/053770 A1 | 5/2006 |
| WO | WO 2006/135437 A2 | 12/2006 |

OTHER PUBLICATIONS

Anthony et al., "Rapid Diagnosis of Bacteremia by Universal Amplification of 23S Abosomal DNA Followed by Hybridization to an Oligonucleotide Array", *Journal of Clinical Microbiology*, vol. 38 (2000), pp. 781-788.
Apostolidis et al., "Genetic Differentiation and Phylogenetic Relationships Among Greek Salmo Trutta L. (brown trout) Populations as Revealed by RFLP Analysis of PCR Amplified Mitochondrial DNA Segments", *Heredity*, vol. 77(6) (1996), pp. 608-618, abstract only.
Bier et al., "Feature-Size Limitations of Microarray Technology—A Critical Review," *Fresenius J. Anal. Chem.*, vol. 371 (2) (2001), pp. 151-156.
Bier et al., "Real-Time Analysis on Microarrays", *Analytical and Bioanalytical Chemistry*, vol. 378 (1) (2004), pp. 52-53.
Boyer et al., "Photothermal Imaging of Nanometer-Sized Metal Particles Among Scatterers", *Science*, vol. 297 (2002), pp. 1160-1163.
Caruso et al., "Quartz Crystal Microbalance Study of DNA Immobilization and Hybridization for Nucleic Acid Sensor Development", *Anal. Chem.*, vol. 69 (1) (1997), pp. 2043-2049.
Cognet et al., "Single Metallic Nanoparticle Imaging for Protein Detection in Cells," *PNAS*, vol. 100 (20) (2003), pp. 11350-11355.
Fodor et al., "Multiplexed Biochemical Assays with Biological Chips", *Nature*, vol. 364(1993), pp. 555-556.
Guo et al., "Direct Fluorescence Analysis of Genetic Polymorphisms by Hybridization with Oligonucleotide Arrays on Glass Supports", *Nucleic Acids Research*, vol. 22 (1994), pp. 5456-5465.
Guschin et al., "Oligonucleotide Microchips as Genosensors for Determinative and Environmental Studies in Microbiology", *Appl Environ Microbiol*, vol. 63(6) (1997), pp. 2397-2402.
Han et al., "Quantum-Dot-Tagged Microbeads for Multiplexed Optical Coding of Biomolecules", *Nature Biotechnology*, vol. 19 (2001), pp. 631-635.
Hutchinson, "Evanescent Wave Biosensors. Real-Time Analysis of Biomolecular Interactions", *Molecular Biotechnology*, vol. 3 (1) (1995), pp. 47-54.

International Preliminary Examination Report from co-pending PCT/BE01/00053 dated Mar. 17, 2003, which claims priority to the same European applications as the above-identified application.
International Search Report from priority European patent application No. EP00870055.1, filed Mar. 24, 2000.
Lehr et al., "Modeling and Experimental Verification of the Performance of TIRF-Sensing Systems for Oligonucleotide Microarrays Based on Bulk and Integrated Optical Planar Waveguides," *Sensors and Actuators B*, vol. 92 (3) (2003), pp. 303-314.
Lehr et al., "Real-Time Detection of Nucleic Acid Interactions by Total Internal Reflection Fluorescence", *Analytical Chemistry*, vol. 75(10) (2003), pp. 2414-2420.
Letter from Jose Remacle to Eric Van Malderen, dated Feb. 24, 2000.
de Longueville et al., "Gene Expression Profiling of Drug Metabolism and Toxicology Markers Using a Low-Density DNA Microarray", *Biochemical Pharmacology*, vol. 64 (2002), pp. 137-149.
Martineau et al., "Correlation Between the Resistance Genotype Determined by Multiplex PCR Assays and the Antibiotic Susceptibility Patterns of *Staphylococcus aureus* and *Staphylococcus epidermidis*", *Antimicrob Agents Chemother*, vol. 44(2) (2000), pp. 231-238.
Maskos, Uwe and Southern, Edwin M., "Oligonucleotide Hybridizations on Glass Supports a Novel Linker for Oligonucleotide Synthesis and Hybridization Properties of Oligonucleotides Synthesized in situ", *Nucleic Acids Research*, vol. 20(7) (1992), pp. 1679-1684.
McKendry et al., "Multiple Label-Free Biodetection and Quantitative DNA-Binding Assays on a Nanomechanical Cantilever Array," *PNAS*, vol. 99 (15) (2002), pp. 9783-9788.
McQuain et al., "Chaotic Mixer Improves Micoarray Hybridization," *Analytical Biochemistry*, Academmic Press, vol. 325 (2) (2004), pp. 215-226.
Moreno-Hagelsieb et al., "Sensitive DNA Electrical Detection Based on Interdigitated Al/Al2O3 Microelectrodes," *Sensors and Actuators B*, vol. 98 (2004), pp. 269-274.
Musser JM, "Antimicrobial Agent Resistance in Mycobacteria: Molecular Genetic Insights", *Clinical Microbiol Rev.*, vol. 8(4) (1995), pp. 496-514.
Nice et al., "Instrumental Biosensors: New Perspectives for the Analysis of Biomolecular Interactions", *Bioassays*, vol. 21(4) (1999), pp. 339-352.
Office Action from priority U.S. Appl. No. 10/056,229, dated Feb. 25, 2003.
Office Action from priority U.S. Appl. No. 10/056,229, dated Jan. 2, 2004.
Office Action from priority U.S. Appl. No. 09/817,014, dated Nov. 27, 2002.
Office Action from priority U.S. Appl. No. 09/817,014, dated Sep. 11, 2003.
Office Action from priority U.S. Appl. No. 09/817,014, dated Sep. 27, 2004.
Office Action from priority U.S. Appl. No. 09/817,014, dated Mar. 18, 2005.
Ozsoz et al., "Electrochemical Genosensor Based on Colloidal Gold Nanoparticles for the Detection of Factor V Leiden Mutation Using Disposable Pencil Graphite Electrodes," *Anal. Chem.*, vol. 75 (9) (2003), pp. 2181-2187.
Remacle et al., U.S. Appl. No. 09/817,014, filed Mar. 23, 2001.
Remacle et al., U.S. Appl. No. 10/056,229, filed Jan. 23, 2002.
Rose et al., "Consensus-Degenerate Hybrid Oligonucleotide Primers for Amplification of Distantly Related Sequences," *Nucleic Acids Research*, vol. 26(7) (1998), pp. 1628-1635.
Schena, M., et al., "Parallel Human Genome Analysis: Microarray-based Expression Monitoring of 1000 Genes", *Proc. Natl. Acad Sci. U.S.A.*, vol. 93 (1996), pp. 10614-10619.
Schwonbeck et al., "Cohort Analysis of a Single Nucleotide Polymorphism on DNA Chips", *Biosensors & Bioelectronics*, vol. 20 (5) (2004), pp. 956-966.
Shchepinov, M.S. et al., "Steric Factors Influencing Hybridization of Nucleic Acids to Oligonucleotide Arrays", *Nucleic Acids Research*, vol. 25 (1997), pp. 1155-1161.
Stimpson et al., "Real-Time Detection of DNA Hybridization and Melting on Oligonucleotide Arrays by Using Optical Wave Guides", *Proc. Natl. Acad. Sci. USA*, vol. 92 (2003), pp. 6379-6383.

Thiel et al., "In Situ Surface Plamon Resonance Imaging Detection of DNA Hybridization to Oligonucleotide Arrays on Gold Surfaces," *Anal. Chem.*, vol. 69 (24) (1997), pp. 4948-4956.

Van Ness et al., "A Versatile Solid Support System for Oligodeoxynucleotide Probe-Based Hybridization Assays", *Nucleic Acids Research*, vol. 19 (12) (1991), pp. 3345-3350.

Vannuffle et al., "Combined Discrimination Between *Staphylococcus* Species and Identification of Methicillin Resistance by a Sandwich Enzyme-Linked Oligo Sorbent Assay", *Abstracts of the Interscience Conference on Antimicrobial Agents and Chemotherapy*, vol. 39 (1999), pp. 208 [XP001053081].

Wei et al., "Monitoring DNA Hybridization on Alkyl Modified Silicon Surface Through Capacitance Measurement", *Biosensors and Bioelectronics*, vol. 18 (9) (2003), pp. 1157-1163.

Wetmur et al., "Kinetics of Renaturation of DNA", *J Mol Biol.*, vol. 31 (1968), pp. 349-370.

Wu, Dan Y and R. B. Wallace, "The Ligation Amplification Reaction (LAR)—Amplification of Specific DNA Sequences Using Sequential Rounds of Template-Dependent Ligation", *Genomic.*, vol. 4 (1989), pp. 560-569.

Yershov et al., "DNA Analysis and Diagnostics on Oligonucleotide Microchips", *Proc Natl Acad Sci U.S.A.*, vol. 93(10) (1996), pp. 4913-4918.

Zammatteo et al., "Comparison Between Microwell and Bead Supports for the Detection of Human Cytomegalovirus Amplicons by Sandwich Hybridization", *Analytical Biochemistry*, vol. 253 (1997), pp. 180-189.

Zammatteo N et al: "New Chips for Molecular Biology and Diagnostics" Biotechnology Annual Review, vol. 8, 2002, pp. 85-101.

Raymond J R et al: "Immunohistochemical Mapping of Cellular and Subcellular Distribution of 5-HT-1A Receptors in Rat and Human Kidneys", American Journal of Physiology, American Physiological Society, Bethesda, MD, US, vol. 264, No. 1, Part 2, Jan. 1993, pp. F09-F19.

McCabe K M et al: "Bacterial Species Identification after DNA Amplification with a Universal Primer Pair", Molecular Genetics and Metabolism, vol. 66, 1999, pp. 205-211.

Peytavi R et al: "Correlation between Microarray DNA Hybridization Efficiency and the Position of Short Capture Probe on the Target Nucleic Acid" BioTechniques, vol. 39, 2005, pp. 89-96.

European Search Report: EP 06 11 4109.

International Search Report: PCT/EP2007/054696.

* cited by examiner

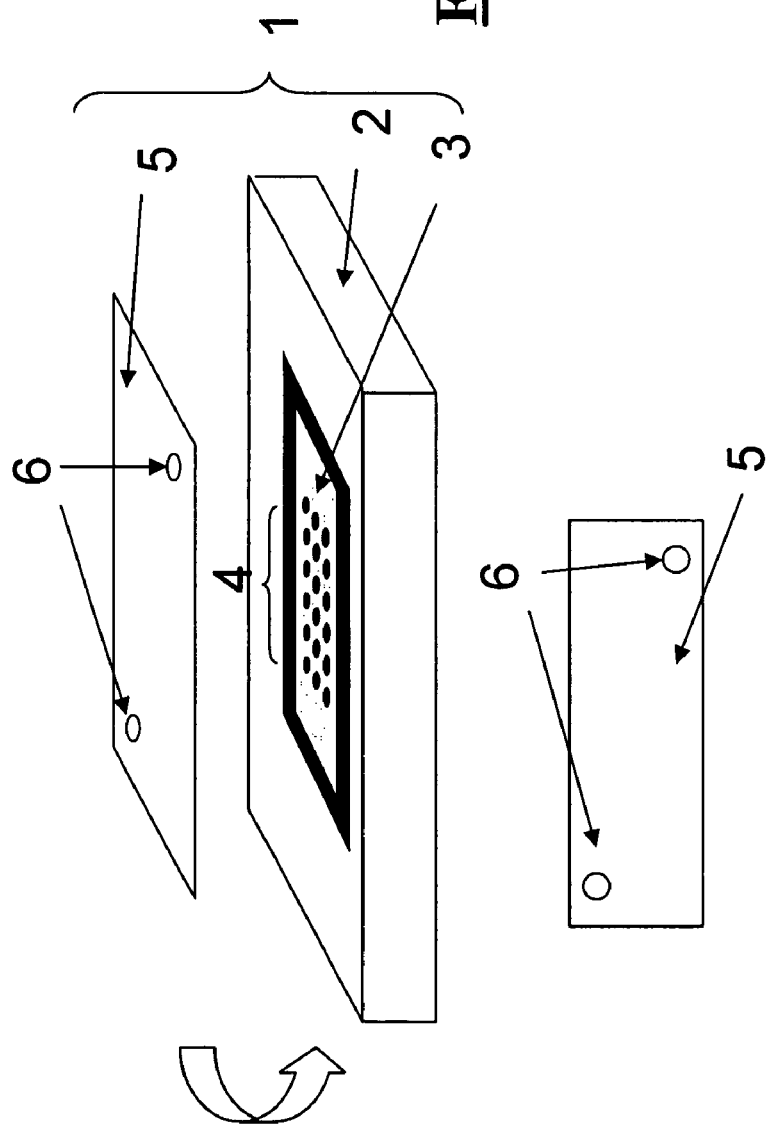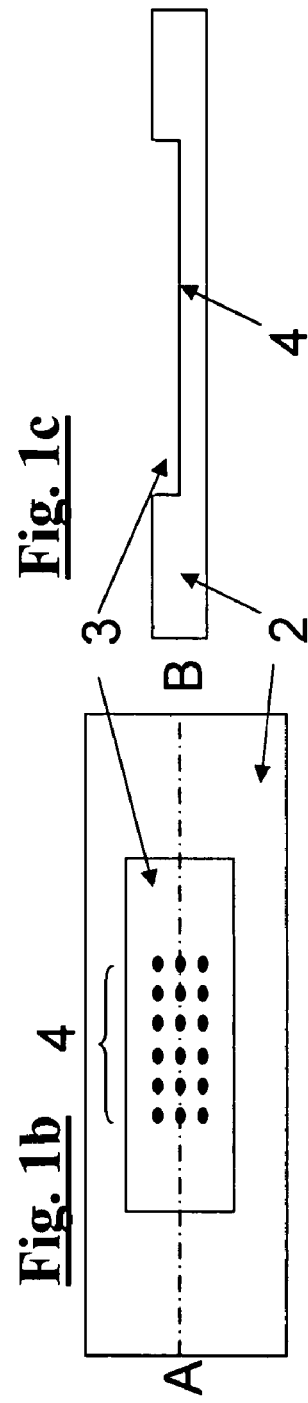

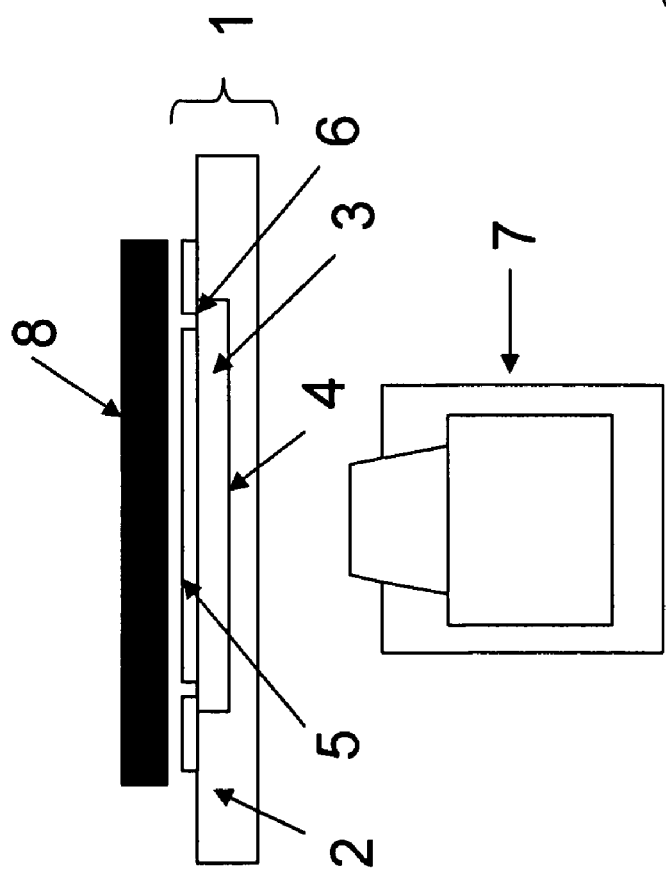
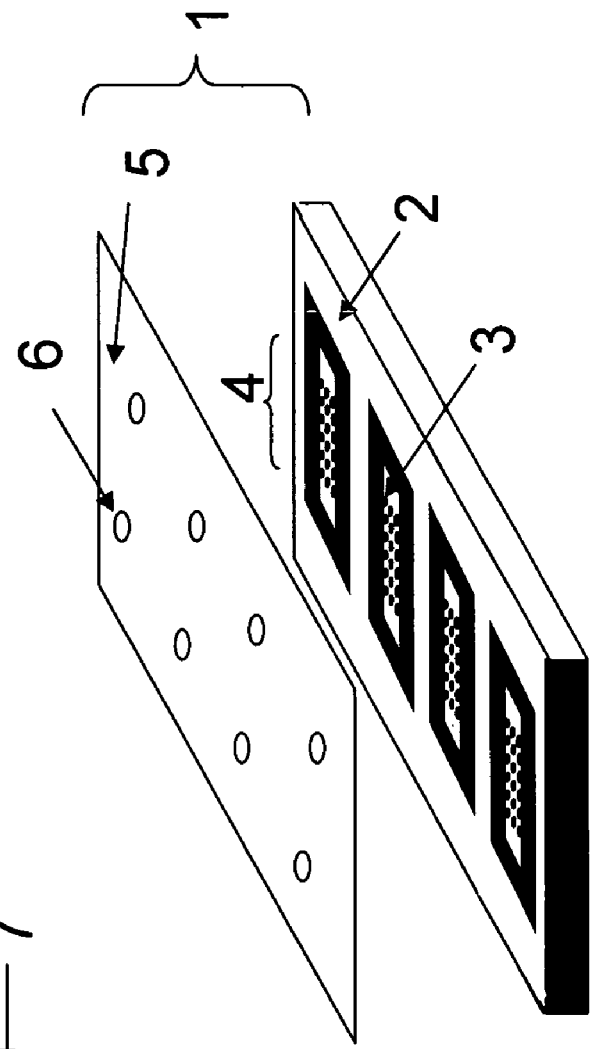

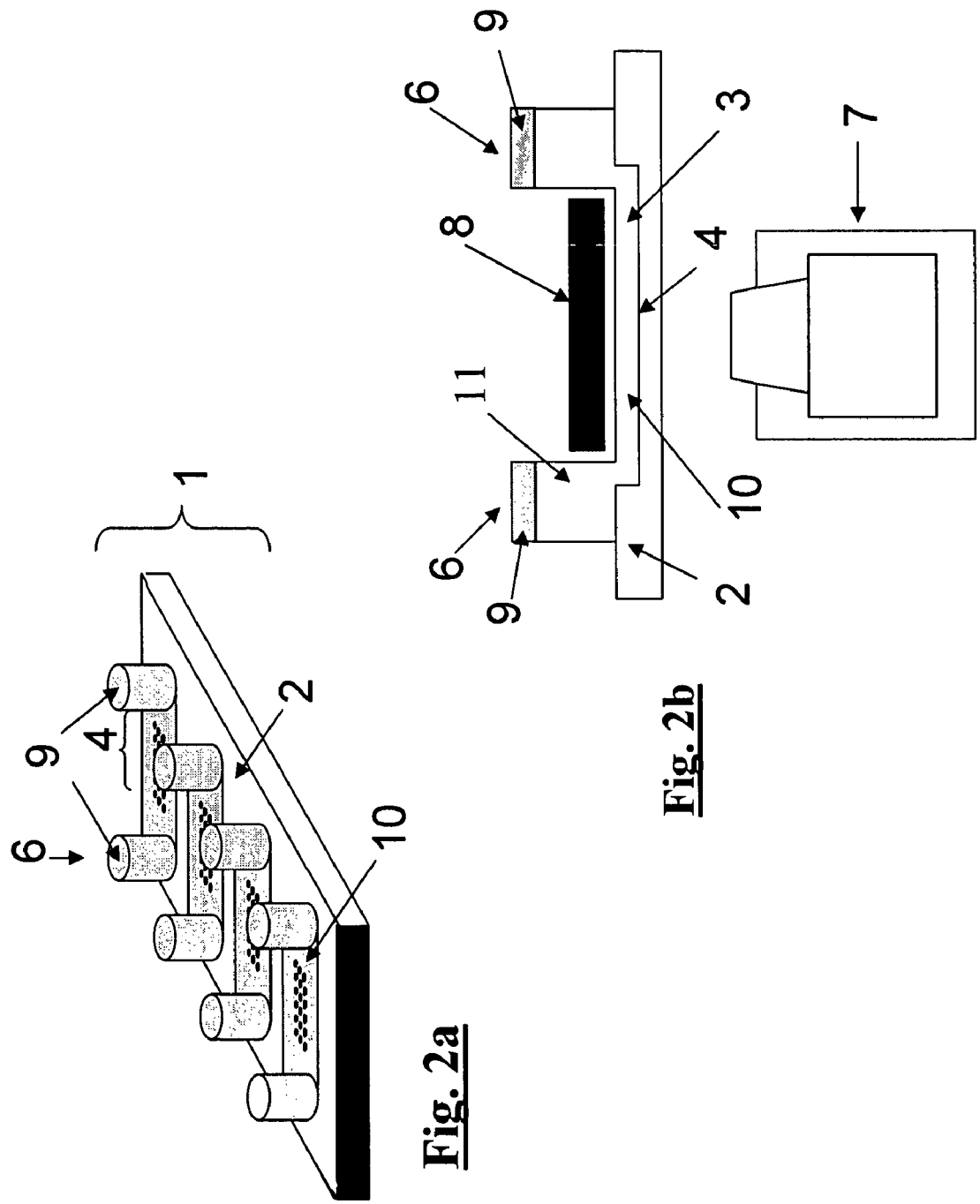

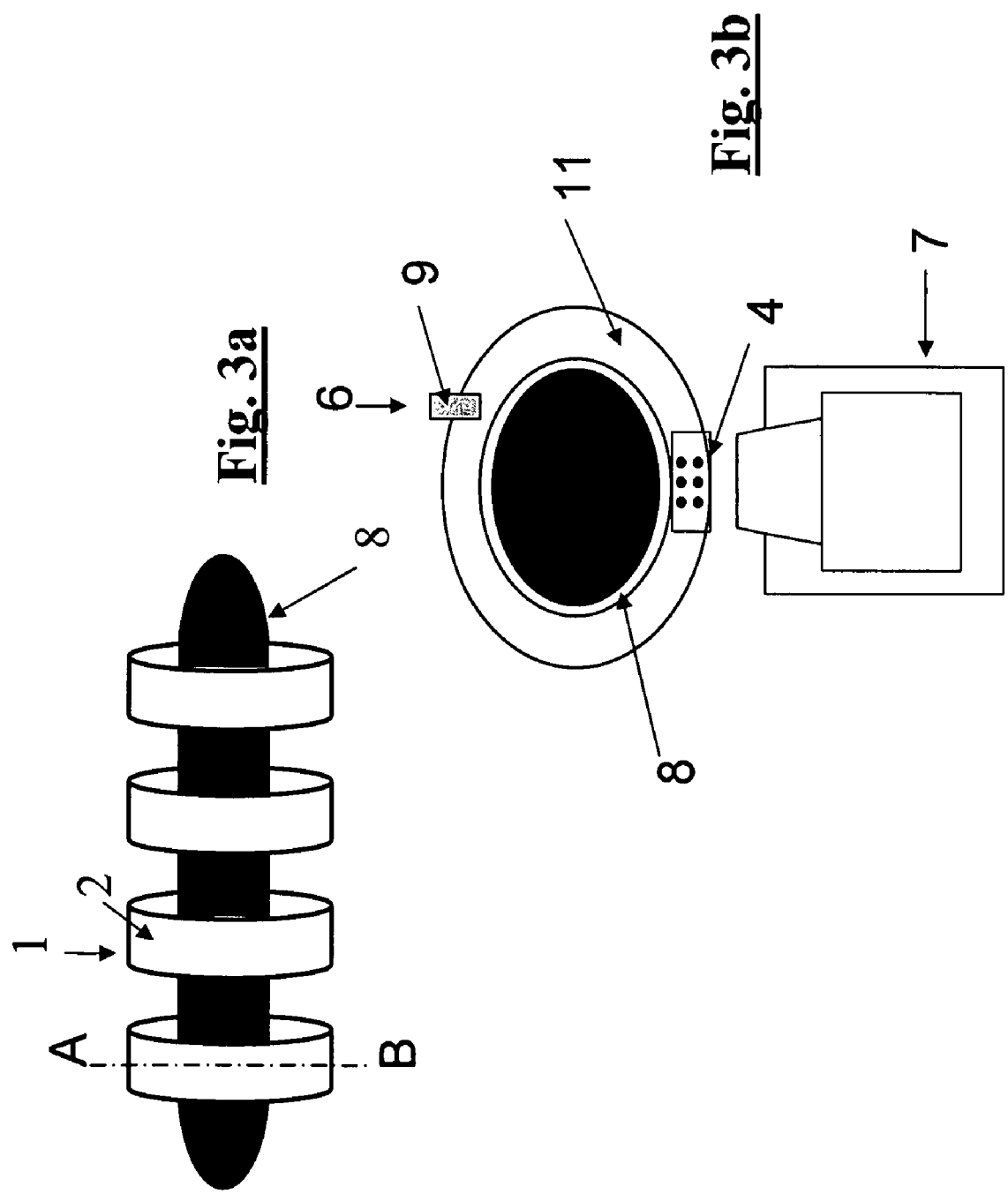

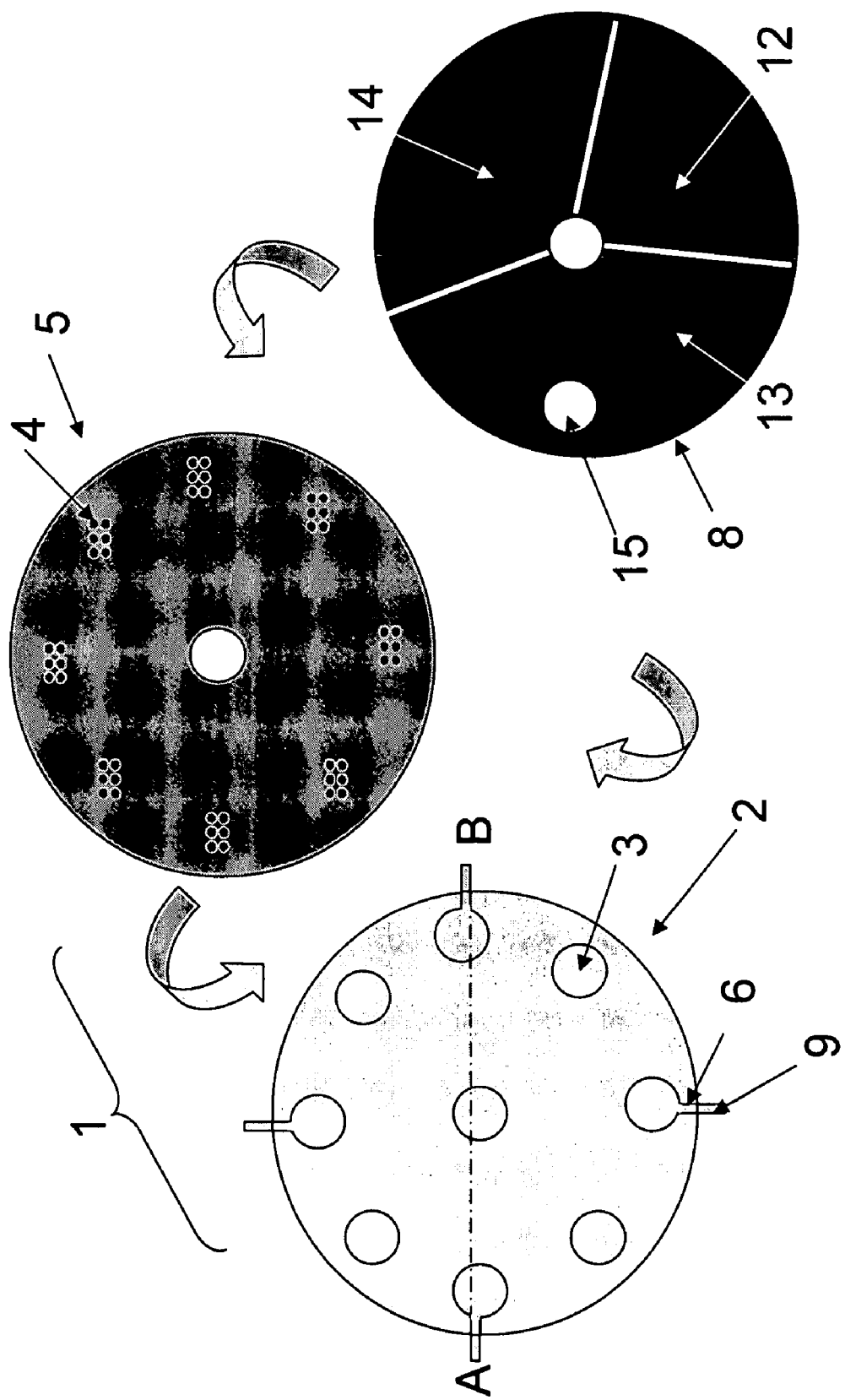

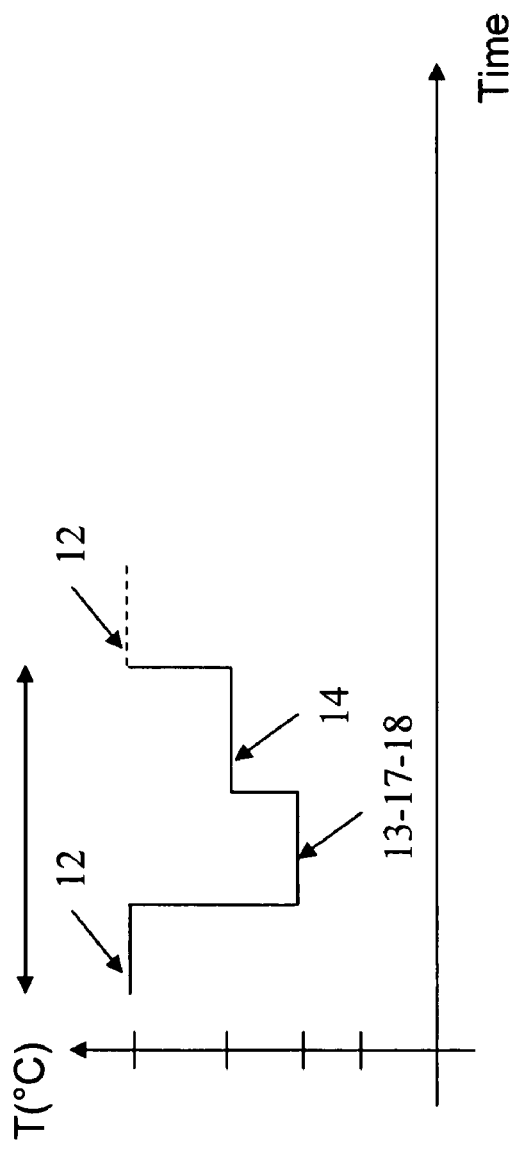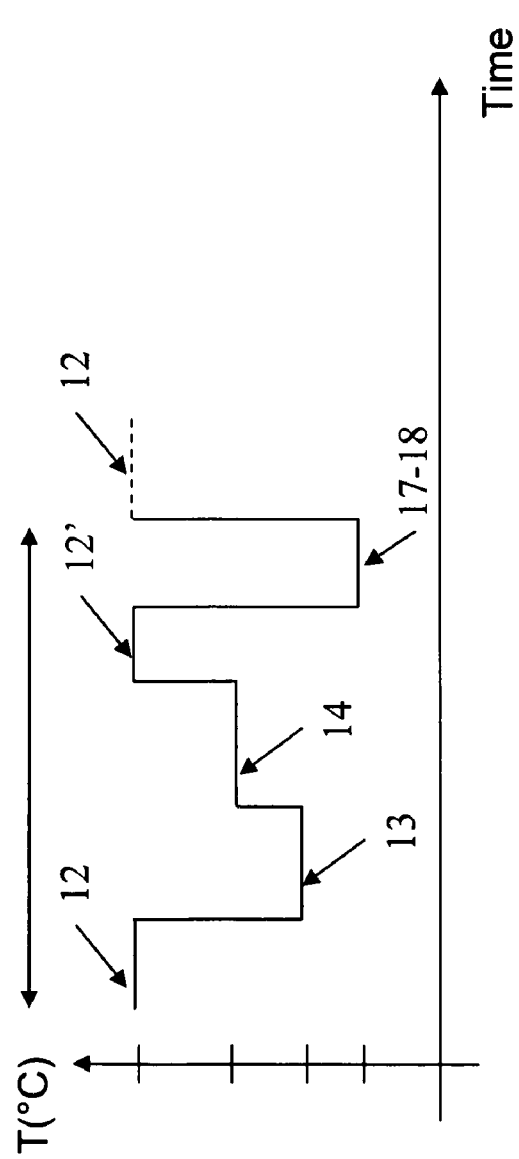

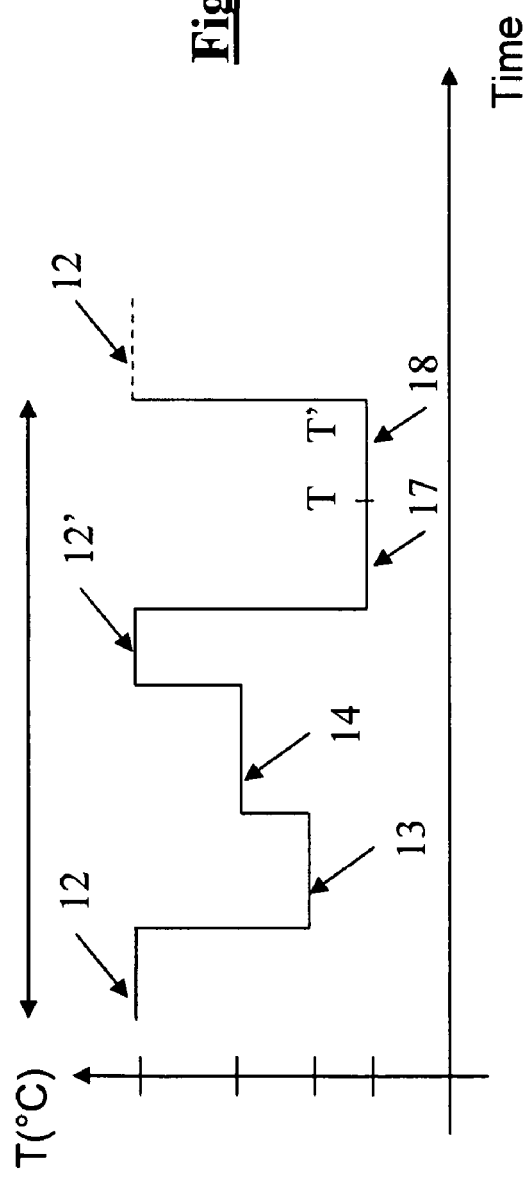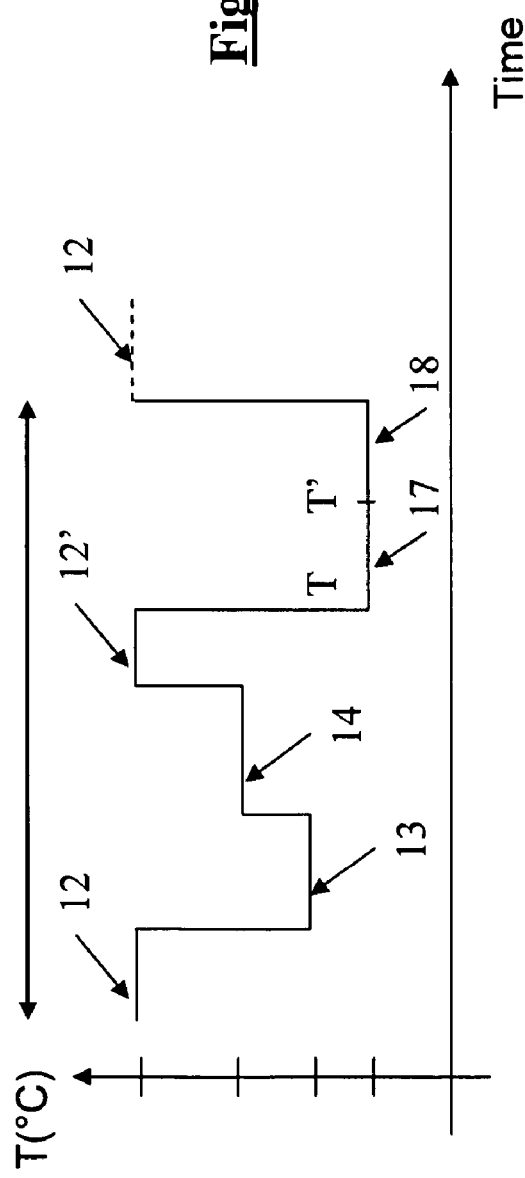

SEQUENCE LISTING

```
<160> NUMBER OF SEQ ID NOS: 15

<210> SEQ ID NO 1
<211> LENGTH: 90
<212> TYPE: DNA
<213> ORGANISM: Artificial Sequence
<220> FEATURE:
<223> OTHER INFORMATION: Synthetic

<400> SEQUENCE: 1
aaagttgagt ccatttgtga tgctagaaaa gttggaactt tcttgaacgt ctcctatatg      60
tcatacatga ataggttgat tttactgtac                                       90

<210> SEQ ID NO 2
<211> LENGTH: 95
<212> TYPE: DNA
<213> ORGANISM: Artificial Sequence
<220> FEATURE:
<223> OTHER INFORMATION: Synthetic

<400> SEQUENCE: 2
ataaaaaagt gggtcttaga aataaatttc gaagtgcaat aattattatt cacaacattt      60
cgatttttgc aactacttca gttcactcca aatta                                 95

<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
aactgctgga cttattttag gtaagag                                          27
```

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
cttgtcatgg ggaaatcagg tatcca                                          26

<210> SEQ ID NO 5
<211> LENGTH: 321
<212> TYPE: DNA
<213> ORGANISM: Artificial Sequence
<220> FEATURE:
<223> OTHER INFORMATION: Synthetic

<400> SEQUENCE: 5
tagccctctc acatttatga agcaagcccc acttattccc cattcttcct agttttctcc     60
tcccaggaac tgggccaact cacctgagtc accctacctg tgcctgaccc tacttctttt    120
gctcttagct gtctgctcag acagaacccc tacatgaaac agaaacaaaa acactaaaaa    180
taaaaatggc catttgcttt ttcaccagat ttgctaattt atcctgaaat ttcagattcc    240
cagagcaaaa taattttaaa caaaggttga gatgtaaaag gtattaaatt gatgttgctg    300
gactgtcata gaaattacac c                                             321

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
ggtggggaga aggtcaaggt a                                              21

<210> SEQ ID NO 7
<211> LENGTH: 28
<212> TYPE: DNA
<213> ORGANISM: Artificial Sequence
<220> FEATURE:
<223> OTHER INFORMATION: Synthetic

<400> SEQUENCE: 7
ttaatcaatg gtgtacttag cttaagta                                       28

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
tgaccaaaag gtttggaaaa cgtgca                                         26

<210> SEQ ID NO 9
<211> LENGTH: 25
<212> TYPE: DNA
<213> ORGANISM: Artificial Sequence
<220> FEATURE:
<223> OTHER INFORMATION: Synthetic

```
<400> SEQUENCE: 9
actgccaagg ttgaaaagct catgg                                              25

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
tctgaggtag tagcggctat cgatt                                              25

<210> SEQ ID NO 11
<211> LENGTH: 28
<212> TYPE: DNA
<213> ORGANISM: Artificial Sequence
<220> FEATURE:
<223> OTHER INFORMATION: Synthetic

<400> SEQUENCE: 11
gattgatgca acaagtttat tgatggac                                           28

<210> SEQ ID NO 12
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: N = A,G,T, or C; D = G,A, or T; and R = A, or G

<400> SEQUENCE: 12
gcngcdgcra tgcgttatac                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: H = A,T, or C; Y = C, or T; and K = G, or T

<400> SEQUENCE: 13
gaacchykac ctgtttcata                                                    20

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
ctaaagtcca ggaagagatt gaacg                                              25

<210> SEQ ID NO 15
<211> LENGTH: 27
<212> TYPE: DNA
<213> ORGANISM: Artificial Sequence
```

```
<220> FEATURE:
<223> OTHER INFORMATION: Synthetic

<400> SEQUENCE: 15
cagagtgttg atttgacaag attttac                                          27
```

IDENTIFICATION AND QUANTIFICATION OF A PLURALITY OF BIOLOGICAL (MICRO)ORGANISMS OR THEIR COMPONENTS

CROSS REFERENCE TO RELATED APPLICATIONS

This application is a continuation-in-part of U.S. Ser. No. 11/436,383, filed May 17, 2006, which is a continuation-in-part of U.S. Ser. No. 10/056,229, filed Jan. 23, 2002, U.S. Pat. No. 7,202,026, which is a continuation-in-part of U.S. Ser. No. 09/817,014, filed Mar. 23, 2001, now U.S. Pat. No. 7,205,104, which claims priority of European patent application serial no. EP00870204.5, filed Sep. 15, 2000, and European patent application serial no. EP00870055.1, filed Mar. 24, 2000, each of which is hereby incorporated by reference herein in its entirety. This application is also a continuation-in-part of PCT/EP2005/012383, filed Nov. 18, 2005, which claims priority of U.S. Ser. No. 10/991,087, filed Nov. 18, 2004, each of which is hereby incorporated by reference herein in its entirety.

BACKGROUND OF THE INVENTION

1. Field of the Invention

The present invention relates to a process for conducting real-time PCR, and to a kit comprising reagents and means and apparatus for implementing the process of the invention. The process is suitable for the identification, detection and/or quantification of a large number of (micro)organisms of different groups (classes, family, genus, species, individual among other ones) by their identification or the identification of a component thereof on a same array in real time amplification.

The invention is especially suited for the simultaneous identification and/or quantification of groups and sub-groups of (micro)organisms or related genes present in the same biological sample.

The present invention also provides a simplified process for detecting and identification of any of the search (micro) organisms or genes together with their quantification.

2. Description of the Related Art

Identification of an organism or microorganisms can be performed based on the presence in their genetic material of specific sequences. Identification of a specific organism can be performed easily by amplification of a given sequence of the organism using specific primers and detecting or identifying the amplified sequence.

However, in many applications especially in diagnostic, possible organisms present in biological samples are numerous and belong to different families, genus, species, subspecies or even individuals. Amplification of each of the possible organisms is difficult and expensive. A simple method is thus required for such multi-parametric, multi-levels analysis.

Amplification of a given sequence is performed by several methods such as the polymerase chain reaction (PCR) (U.S. Pat. Nos. 4,683,195 and 4,683,202, each of which is hereby incorporated by reference herein in its entirety), ligase chain reaction (LCR) (Wu and Wallace, 1989, Genomics 4: 560-569) or the Cycling Probe Reaction (CPR) (U.S. Pat. No. 5,011,769, which is hereby incorporated by reference herein in its entirety) which are the most common. One particular way to detect for the presence of a given sequence and thus of a particular organism is to follow the appearance in solution of amplicons during the amplicon cycles. The method is called the real time PCR (sometimes referred to as "RT-PCR"). A fluorescent signal appears in solution when the amplicons are formed and the amplification is considered as positive when reaching a threshold.

Detecting the amplicons can also be performed after the amplification by methods based on the specific recognition of amplicons to complementary sequences immobilized on a solid support. The first supports used for such hybridization were the nitrocellulose or nylon membranes. However, the methods were miniaturized and new supports such as conducting surfaces, silica, and glass were proposed together with the miniaturization of the detection process. Micro-arrays or DNA Chips are used for multiple analyses of DNA or RNA nucleotide sequences specific to an organism either after an amplification step (PCR) or after a reverse transcription into a cDNA and amplification (RT-PCR). The target sequences to be detected are labeled during the amplification or copying step and are then detected, and possibly quantified, on arrays. The presence of a specific target sequence on the arrays is indicative of the presence of a given gene or DNA sequence in the sample, and thus of a given organism, which may then be identified. The problem of detection becomes difficult when several sequences are homologous to each other, but have to be specifically discriminated upon the same array. It is desirable to solve this technical problem to use arrays for such diagnostic purposes, since organisms or micro-organisms of interest are often very similar to others on a taxonomic basis and present almost identical DNA sequences.

The Company Affymetrix Inc. has developed a method for direct synthesis of oligonucleotides upon a solid support, at specific locations by using masks at each step of the processing. Said method comprises the addition of a nucleotide on growing synthesized oligonucleotides in order to obtain the desired sequences at the desired locations. This method is derived from the photolithographic technology and is coupled with the use of photoprotective groups, which are released before a new nucleotide is added (U.S. Pat. No. 5,510,270, which is hereby incorporated by reference herein in its entirety). However, only small oligonucleotides are present on the surface, and said method finds applications mainly for sequencing or identifying a pattern of positive spots corresponding to each specific oligonucleotide bound on the array. The characterization of a target sequence is obtained by cutting this polynucleotide into a small oligonucleotides and comparison of the hybridization pattern with a reference sequence. Said technique was applied to the identification of *Mycobacterium tuberculosis* rpoB gene (WO 97/29212, which is hereby incorporated by reference herein in its entirety), wherein the capture molecule comprises less than 30 nucleotides and from the analysis of two different sequences that may differ by a single nucleotide (the identification of SNPs or genotyping). Small capture oligonucleotide sequences (having a length comprised between 10 and 20 nucleotides) are preferred since the discrimination between two oligonucleotides differing in one base is higher, when their length is smaller.

The method is complicated by the fact that it cannot directly detect amplicons resulting from genetic amplification (PCR). A double amplification is performed with primer(s) bearing a T3 or T7 sequences and then a reverse transcription with a RNA polymerase. These RNA are cut into pieces of about 40 bases before being detected on an array (example 1 of WO 97/29212, which is hereby incorporated by reference herein in its entirety). Each sequence requires the presence of 10 capture molecules and 10 control nucleotide sequences to be identified on the array. The reason for this complex procedure is that long DNA or RNA fragments hybridize very slowly on small oligonucleotide capture molecules present on the surface. Said methods are therefore not suited for the detection of homologous sequences, since the homology varies along the sequences and so part of the pieces will hybridize on the same capture molecules. Therefore, software for the interpretation of the results is incorporated in the method for allowing interpretation of the obtained data. The main reason not to perform a single hybridization of the amplicons on the array is that the amplicons will re-hybridize in solution much faster than hybridize on the small capture molecules of the array.

A consequence of such constraints is that polynucleotides are analyzed on oligonucleotides based arrays, only after being cut into oligonucleotides. For gene expression array which is based on the detection of cDNA copy of the mRNA, the problem still exist but is less acute since the cDNA is single stranded. The fragments are also cut into smaller species and the method requires the use of several capture oligonucleotide sequences in order to obtain a pattern of signals which attest the presence of a given gene. Said cutting also decreases the number of labeled nucleotides, and thus reduces the obtained signal. In the case of cDNA analysis, the use of long capture polynucleotide sequences gives a much better sensitivity to the detection. In many gene expression applications, the use of long capture molecules is not a problem, when cDNAs to be detected originate from genes having different sequences, since the difference in the sequence is sufficient in order to avoid cross reactions between them even on a sequence longer than 100 bases so that polynucleotides can be used as capture molecules. However, long capture molecules give the required sensitivity but they will hybridize to other homologous sequences.

The detection of Single Nucleotide Polymorphism in the DNA is just one particular aspect of the detection of homologous sequences. The use of arrays has been proposed to discriminate two sequences differing by one nucleotide at a particular location of the sequence. Since DNA or RNA sequences are in low copy numbers, their sequences are first amplified so that double stranded sequences are analyzed on the array. Several methods have been proposed to detect such a base change in one location. The document WO 97/31256, which is hereby incorporated by reference herein in its entirety, proposes the ligation detection reaction between one oligonucleotide probe, which has a target sequence-specific portion and an addressable array-specific portion and a second oligonucleotide probe, having a target sequence-specific portion and a detectable label When the two oligonucleotides are hybridization on the target, they are ligated. After ligation in solution, the labeled product is immobilized on an array by the addressable array-specific portion. The detection of SNP is the basis for polymorphism determination of individual organism, but also for its genotyping, since the genome of individuals differs from each other in the same species or subspecies by said SNPs. The presence of a particular SNP can affect the activities of enzymes, like P450, and make them more or less active in the metabolism of a drug.

The capture oligonucleotide present on the array can also be used as primers for extension once the target nucleotide hybridized. The document WO 96/31622, which is hereby incorporated by reference herein in its entirety, proposes to identify a nucleotide at a given location upon a sequence by elongation of a capture molecule with detectable modified nucleotides in order to detect the given spots, where the target has been bound with the last nucleotide of the capture molecule being complementary of a target sequence at this particular position. The document WO 98/28438, which is hereby incorporated by reference herein in its entirety, proposes to complete several cycles of hybridization-elongation steps to label a spot in order to compensate for a low hybridization yield of the target sequence. This method allows identification of a nucleotide at a given location of a sequence by labeling of a spot of the elongated capture molecule.

Prior to elongation, the capture molecules present on the array can be digested by a nuclease in order to differentiate between matched and the unmatched heteroduplexes (U.S. Pat. No. 5,753,439, which is hereby incorporated by reference herein in its entirety). Use of nuclease for identification of sequences has also been proposed (EP 0721016, which is hereby incorporated by reference herein in its entirety). A second labeled nucleotide sequence complementary of the targets has also been proposed to be added to the hybridized targets and being ligated to the capture molecule if the last nucleotide of the targets is complementary to the targets at this position (WO 96/31622, which is hereby incorporated by reference herein in its entirety).

The document EP 0785280, which is hereby incorporated by reference herein in its entirety, proposes a detection of polymorphism based on the hybridization of the target nucleotides on blocks containing several oligonucleotide sequences differing by one base each and obtain a ratio of intensity for determining which sequences are the perfect hybridization matches.

Using membranes or nylon supports are proposed to increase the sensitivity of the detection of polynucleotides on solid support by incorporation of a spacer between the support and the capture molecules. Van Ness et al. (Nucleic Acids Research, vol. 19, p. 3345, 1991) describe a poly(ethylene-imine) arm for the binding of DNA on nylon membranes. The document EP-0511559, which is hereby incorporated by reference herein in its entirety, describes a hexaethylene glycol derivative as spacer for the binding of small oligonucleotides upon a membrane. When membranes like nylon are used as support, there is no control of the site of binding between the solid support and the oligonucleotides and it was observed that a polydT tail increased the fixation yield and so the resulting hybridization (WO 89/11548, which is hereby incorporated by reference herein in its entirety).

Guo et al. (Nucleic Acids Research, Vol. 22, p. 5456, 1994) teach the use of polydT of 15 bases as spacer for the binding of oligonucleotides on glass with increased sensitivity of hybridization.

The publication of Anthony et al. (Journal of clinical microbiology, Vol. 38, p. 7817, 2000) describes the use of a membrane array for the detection of 23 S ribosomal DNA of various bacterial species after PCR amplification. Targets to detect are rDNA amplified from bacteria by consensus PCR and the detection is obtained on nylon array containing capture molecules for said bacteria and having the capture molecules having between 20 and 30 bases which are covalently linked to the nylon, and there is no control of the portion of the sequence which is available for hybridization. rDNA are multi-copies of DNA which are used in order to compensate for the low detection yield of the method. Also, because of the use of small capture molecules they can only detect individual bacterial species by their specific sequence and not the family or genus.

There is neither an indication nor a suggestion in the state of the art that polynucleotides being longer than oligonucleotides can be used as capture sequences in micro-arrays in order to differentiate a binding between homologous polynucleotides sequences and to permit identification of one target sequence among other species, genus or families of (micro)organisms sequences or components thereof and to detect and/or quantify the presence of the target during the amplification.

Also there is no indication nor suggestion that homologous sequences differing by one nucleotide at one location of the sequence (such as observed in polymorphism analysis) could be detected by hybridization of the amplified sequences on corresponding capture molecules during the amplification.

Prior to the invention, it was unknown that it is possible to identify in a one step process, i.e., an amplification together with a direct hybridization of the amplicons on an array, organisms belonging to the same group, to two groups or more together with the specific identification of the groups as such. Also it was unknown that it was possible to identify organisms belonging to a group and sub-group together with the specific identification of these group and sub-group during the amplification of one of their sequences. Also that such identification could be obtained by using polynucleotide as capture sequences for all detections.

Also it was unknown that polynucleotides longer than oligonucleotides could be used for the identification of homologous polynucleotide sequences differing by one nucleotide present in a particular location of the sequence during their amplification.

Also it was unknown that homologous polynucleotide sequences could be discriminated and detected on an array directly during their amplification with a very high sensitivity because the related art required fragmentation of the amplicons for their detection on small oligonucleotide array. The fragmentation is not compatible with the real time detection since fragmented amplicons could not be amplified any more thus leading to a stop of the amplification.

BRIEF SUMMARY OF THE INVENTION

The present invention is premised in part on the discovery that arrays can be used to obtain a discrimination between a homologous (biological) component (such as a genetic sequence or mRNA) of the same or of different (micro)organisms belonging to several groups together with the identification and/or their quantification of these groups during the amplification step of their sequences.

The present invention provides a process for real-time PCR comprising the steps of:
 a) conducting at least one PCR cycle to form amplicons;
 b) hybridizing the amplicons to immobilized capture molecules;
 c) detecting the hybridized amplicons; and
 d) repeating steps a) b) c) at least once.

The present invention is especially useful in using arrays to discriminate between homologous nucleotide sequences belonging to several groups together with the identification of these groups as such by real time PCR.

The present invention further provides a method for the identification and/or quantification of a part of an organism such as an expressed gene in the form of an mRNA by determination of the gene content by RT-PCR in real time.

In another embodiment the invention provides a diagnostic kit based upon a simplified technology requiring the use of a single or limited number of primer pair(s) in a one step amplification to detect the presence of the specific target or group of target sequence(s) together with the identification (detection and/or quantification) of said specific target or groups of target genetic sequence(s) by recording in a single spot identification upon said micro-array and in the same experimental protocol, said signal being either specific to the organism or the group or sub-group of organisms.

In yet another embodiment the invention provides an apparatus for carrying out the process of the invention.

The present invention also provides means for an identification of organisms differing by single base difference of a given nucleotide sequence by hybridization of their amplified polynucleotide sequences upon arrays in a real time PCR assay.

BRIEF DESCRIPTION OF THE DRAWINGS

FIG. 1a is a representation of a preferred device for performing the real time PCR and detection on a micro-array. The device comprises a carrier (1) made of a support (2) having a cavity (3), comprising an array (4), sealed with a coverslip (5), having an inlet port (6). FIG. 1b is a top view of the device and FIG. 1c represents a side view A-B. FIG. 1d is a representation of the device which is contacted with a temperature control unit (8) for the PCR amplification and with a detection device (7) for the micro-array analysis. FIG. 1e represents a multiplexing of the device of FIG. 1.

FIG. 2a represents a device for performing multiple real time PCR and detection on a micro-array having two chambers (11) with a lid (9) separated by a channel (10) in the form of a cavity bearing the arrays. FIG. 2b is a representation of the device which is contacted with a temperature control unit (8) for the PCR amplification and with a detection device (7) for the micro-array analysis.

FIG. 3a is a representation of a preferred device for performing the real time PCR and detection on a micro-array having several chambers (11) present on a ring and annealed around a temperature control unit (8). The array (4) is positioned in the chamber at a specific location. A lid (9) enables the introduction of solution in the chamber through inlet port (6). FIG. 3b represents a side view A-B of the device when the detection device (7) is included.

FIG. 6a represents a disc having different micro-arrays for the detection of the amplicons during the PCR and having different temperatures along the different parts of the disc. Part with denaturation (12), annealing T° (13), elongation T° (14), window for reading (15).

FIG. 7a is a representation of one amplification/detection cycle in 3 steps: denaturation (12), annealing (13) and elongation (14). The hybridization (17) of the amplicons and their detection (18) on the capture molecules is preferably performed during the annealing step of the cycle. The beginning of the next cycle is represented by a dotted line. FIG. 7b is a representation of the amplification/detection cycle in 5 steps: denaturation (12), annealing (13), elongation (14), denaturation (12') and hybridization (17) detection (18). In this embodiment, the detection of the amplicons is not performed during the PCR cycle but during a specific hybridization step which is preceded by a denaturation step (12) to bring the signal on the capture molecules to zero. The beginning of the next cycle is represented by a dotted line. This embodiment is illustrated in example 2.

FIG. 8 is a representation of one amplification/detection cycle in 6 steps in a specific embodiment of the invention where the capture molecules are in intermittent contact with the PCR solution. The successive steps are: denaturation (12), annealing (13), elongation (14), denaturation (12'), hybridization (17) and detection (18). FIG. 8a represents an embodiment where the capture molecules are immobilized in the reaction chamber preferably at the bottom. They are in contact with the PCR solution during all the steps, except during the detection (18). To reach that purpose, the liquid is moved away from the capture molecules. One embodiment is to turn the chamber upside down before (T) and after (T') the detection step (18). The beginning of the next cycle is represented by a dotted line. FIG. 8b represents an alternative embodiment where the capture molecules are immobilized in the lid (9) of a reaction chamber. They are in contact with the PCR solution only during the step of hybridization (17). To reach that purpose, the chamber is turned upside down before (T) and after (T') the hybridization step (17). The beginning of the next cycle is represented by a dotted line.

DETAILED DESCRIPTION OF ILLUSTRATIVE EMBODIMENTS

Figure 4:
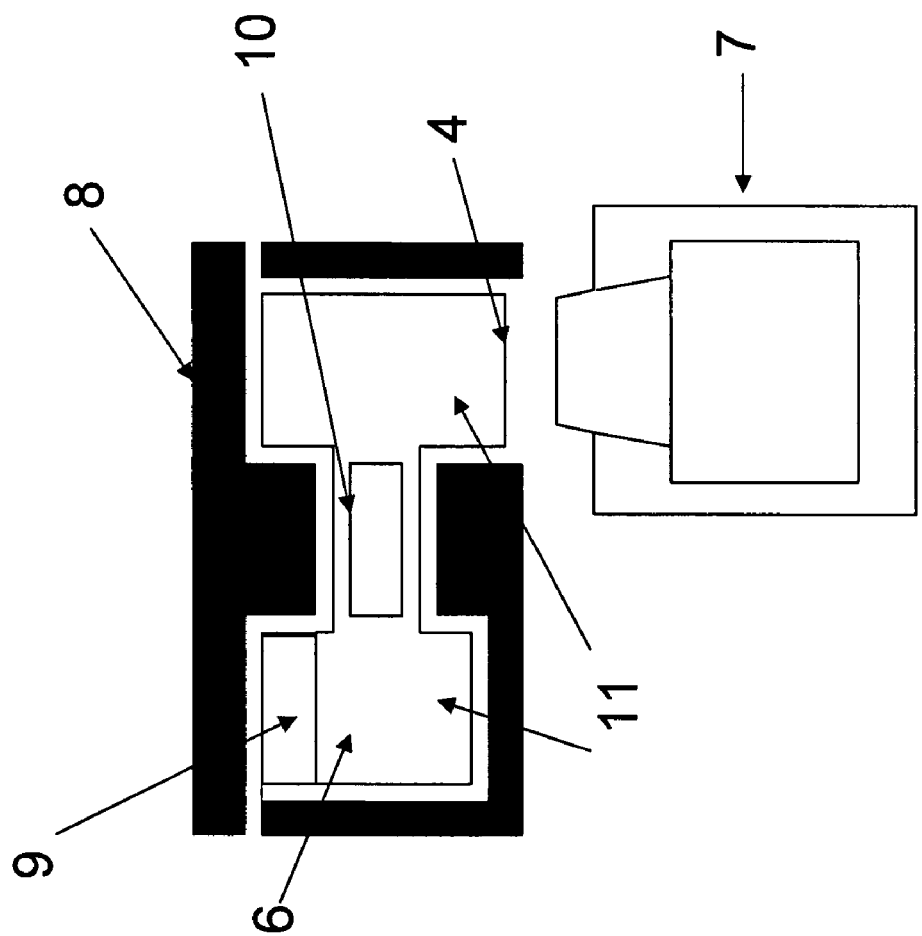
FIG. 4 represents another device for performing the real time PCR and detection on a micro-array having two chambers (11) with one chamber bearing the array (4). Fluid can be transferred from one chamber to the other one through channels (10).
Figure 5B:
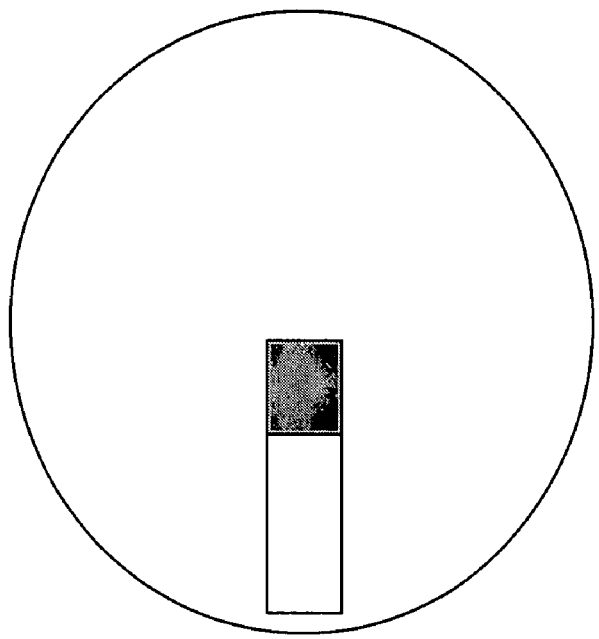
FIG. 5a represents a preferred device for performing the real time PCR and detection on a micro-array having an asymmetric chamber (11) with one part having the array (4). The device is preferably part of a disk support to allow an easy centrifugation of the device (FIG. 5b). The steps of the method in which the device is used are presented in FIG. 5a. In step 1, a solution containing the nucleotide molecules and reagents for amplification and labeling are introduced into a first compartment of the reaction chamber (11). Capture molecules (4) are immobilized at the top of the second compartment of the reaction chamber (11). In step 2, the reaction chamber is sealed with a lid (9) and the PCR amplification is performed in the first compartment of the reaction chamber (11) which is in contact with a temperature control unit (8). In step 3, the reaction chamber (11) is centrifuged and flipped in order to contact the solution containing the labeled target molecules with the capture molecules (4) immobilized in the second compartment. In step 4, the chamber (11) is inverted back, and the bound labeled target molecules are measured through a window by the detector (7).
Figure 5A:
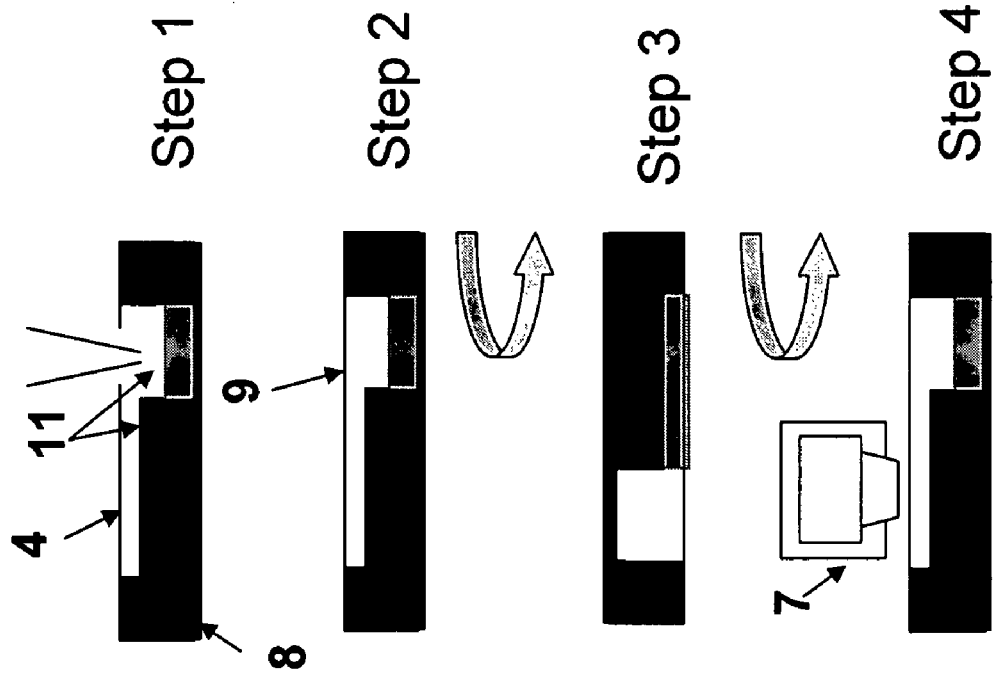
Figure 6B:
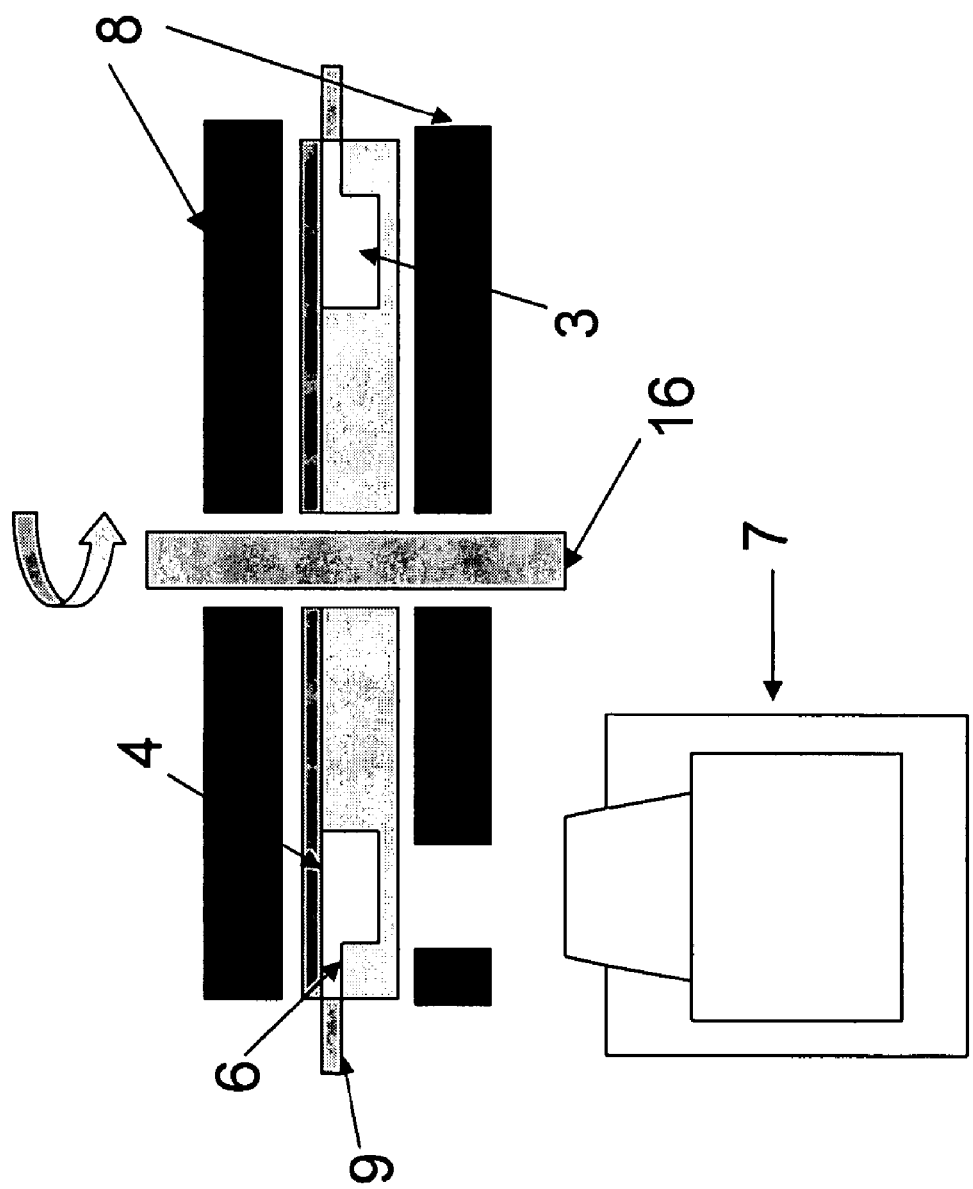
FIG. 6b represent a side view A-B of device of FIG. 6a which is contacted with a temperature control unit (8) for the PCR amplification and with a detection device (7) for the micro-array analysis. The disc rotates on its axe by the means of a step motor (16).

The following is a description of certain embodiments of the invention, given by way of example only and with reference to the drawings.

Definitions

The terms "nucleic acid, oligonucleotide, array, nucleotide sequence, target nucleic acid, bind substantially, hybridizing specifically to, background, quantifying" are the ones described in the international patent application WO 97/27317, which is hereby incorporated by reference herein in its entirety. The term polynucleotide refers to nucleotide or nucleotide like sequences being usually composed of DNA or RNA sequences. Oligonucleotides are considered as small sequences being usually of between 15 and 40 nucleotides long and in any way lower than 100 nucleotides long.

The terms "nucleotide triphosphate, nucleotide, primer sequence" are those described in the document WO 00/72018 and WO 01/31055, each which is hereby incorporated by reference herein in its entirety.

References to nucleotide(s), polynucleotide(s) and the like include analogous species wherein the sugar-phosphate backbone is modified and/or replaced, provided that its hybridization properties are not destroyed. By way of example the backbone may be replaced by an equivalent synthetic peptide, called Peptide Nucleic Acid (PNA).

The terms "homologous genetic sequences" mean amino acid or nucleotide sequences having a percentage of amino acids or nucleotides identical at corresponding positions which is higher than in purely random alignments. They are considered as homologous when they show a minimum of homology (or sequence identity) defined as the percentage of identical nucleotides or amino acids found at each position compared to a total of nucleotides or amino acids, after the sequences have been optimally aligned taking into account additions or deletions (like gaps) in one of the two sequences to be compared. Genes coding for a given protein but present in genetically different sources like different organisms are usually homologous. Also in a given organism, genes coding for proteins or enzymes of the same family (Interleukins, cytochrome b, cytochrome P450). The degree of homology (or sequence identity) can vary a lot as homologous sequences may be homologous only in one part, a few parts or portions or all along their sequences. The parts or portions of the sequences that are identical in both sequences are said conserved. The sequences having a significant part of the sequence being identical are considered as homologous. This part is at least 10 consecutive nucleotide long and better 15 and even better 20. Protein domains which present a conserved three dimensional structure are usually coded by homologous sequences and even often by a unique exon. The sequences showing a high degree of invariance in their sequences are said to be highly conserved and they present a high degree of homology.

The terms "group," "sub-group," and "sub-sub-group" when used herein in the context of classification of biological organisms refer to the taxus, kingdom, branches, classes, orders, families, genus, species, sub-species, varieties or individuals. These constitute different levels of biological taxonomical organization. Groups also refer to organisms which have some aspects in common, but some genetic differences like for example the GMO plants, transgenic or chimeric animals. For the purpose of this invention, the common aspects have to be reflected into common or homology DNA or RNA sequences and the dissimilarities or differences in DNA sequences. Gene sequences can also be classified in groups and sub-group independently of their organism origins and are as such part of the invention. They will then refer to groups or sub-groups of genes which belong to a given family such as the cytochrome P450 genes, the protein kinases, the G receptor coupled proteins and others. These genes are homologous to each other as defined here above.

Classification of genes (nucleotide sequences) is used as the basis of molecules paleontology for establishing the classification of organisms into species, genus, family, orders, classes, branches, kingdom and taxus.

"Micro-array" as used herein refers to one or more solid supports on which multiple capture molecules are immobilized in order to be able to bind to the given specific target molecule. The micro-array is preferentially composed of capture molecules present at specifically localized areas on the surface of a single support or within the support or on the substrate covering the support. A specifically localized area is the area of the surface which contains bound capture molecules specific for a determined target molecule. The specific localized area is either known by the method of building the micro-array or is defined during or after the detection. A spot is the area where specific target molecules are fixed on their capture molecules and seen by the detector. In one particular application of this invention, micro-arrays of capture molecules are also provided on different or separate supports as long as the different supports contain specific capture molecules and may be distinguished from each other in order to be able to quantify the specific target molecules. This can be achieved by using a mixture of beads having particular features and being able to be recognized from each other in order to quantify the bound molecules. One bead or a population of beads is then considered as a spot having a capture molecule specific to one target molecule. Also a well being part of a multiwell plate and bearing capture molecules is considered as an array.

Micro-arrays are preferentially obtained by deposition of the capture molecules on the substrate is done by physical means such as pin or "pin and ring" touching the surface, or by release of a micro-droplet of solution by methods such as piezo or nanodispenser. Alternatively, in situ synthesis of capture molecules on the substrate is one of the invention's embodiments with light spatial resolution of the synthesis of oligonucleotides or polynucleotides in predefined locations such as provided by U.S. Pat. Nos. 5,744,305 and 6,346,413.

As used herein, "capture molecule" refers to a molecule, or complex or combination thereof, that is capable of specifically binding to one target molecule, or to a family of target molecules, or to one or more member(s) of a plurality of target molecules, or portion(s) thereof. Typically, one assay comprises a plurality of identical capture molecules capably of specifically binding to a plurality of the target (or family of target) molecules. The capture molecules are preferably nucleic acids being oligonucleotides or polynucleotides which are either synthesized chemically in situ on the surface of the support or laid down thereon. Nucleic acid binding is achieved via base pairing between two polynucleotides, one being the immobilized capture molecule and the other one the target to be detected.

As used herein, the term "label" refers to any marker or group which is detectable directly or indirectly.

As used herein, the term "unlabeled molecule" refers to any molecule in an assay which does not bear or contain the label(s) used for detection and/or quantification in the assay. For example, an immobilized capture molecule used in an assay may include a group that can be detected (e.g., by NMR or GC-MS) but still be "unlabeled," if this detectable group is not used for detection in the assay.

The term "real time PCR" means a method which allows detecting and/or quantifying the presence of the amplicons during the PCR cycles. In the real time PCR, the presence of the amplicons is detected and/or quantified in at least one of the cycles of amplification. The increase of amplicons or signal related to the amount of amplicons formed during the PCR cycles is used for the detection and/or quantification of a given nucleotide sequence in the PCR solution.

The term stable (or constant) and controlled temperature means a temperature which is obtained by a controlled system being a temperature regulation device and which is stable enough to avoid target hybridization rate variation of more than 10% during the time course of a given measurement. Typical stable temperature is a temperature which does not vary by more than 5° C. and preferably by more than 1° C. for at least one min and better 5 min of time period or even better 60 min of time period or even 24 h.

The "amplicon" of the invention means target nucleotide molecules being the result of PCR amplification of a nucleotide molecule present in a biological material.

The term "solution in contact" means in a fluidic form or allowing movement of the liquid. For instance a surface centrifuged or turned upside down is not in fluidic contact even if a thin film of liquid is still covering the surface.

"Intermittent contact" means to be physically in contact or not according to some time frame. In a particular aspect of the invention the PCR solution is in intermittent contact with the capture molecule, means the PCR solution is moved or displaced from the surface having fixed the capture molecules for a given time period (non contact) and then it is moved back to its original position (contact). Preferably more than 95% and preferably more than 99% of the PCR solution is moved or displaced in the reaction chamber. The PCR solution is preferably displaced by gravity drain resulting from a change in orientation of the reaction chamber, preferably rotation, translation, or lateral movement of the reaction chamber.

The present invention is related to a method for identification and/or quantification of a biological organism or part of an organism, in a sample. The method comprises detecting a nucleotide sequence specific to said organism wherein said nucleotide sequence presents a homology with at least two, and preferably at least four other homologous nucleotide sequences from other organisms. The method is preferably preceded by an extraction and/or purification of the genetic material being genomic DNA or the mRNA.

The method comprises the steps of:
a) conducting at least one PCR cycle to form amplicons;
b) hybridizing the amplicons to immobilized capture molecules;
c) detecting the hybridized amplicons; and
d) repeating steps a) b) c) at least once.

Preferably, the PCR cycle comprises the steps of denaturation, annealing, and elongation, whereby the PCR solution is in constant contact with the capture molecules so that the amplicons are hybridized to the capture molecules during the annealing step.

In an alternate embodiment the capture molecules are in intermittent contact with the PCR solution.

As the PCR cycle itself comprises three steps, the process of the invention in one embodiment comprises the following 6 steps:
 a) denaturation;
 b) annealing;
 c) elongation;
 d) denaturation;
 e) hybridization; and
 f) detection.

In one embodiment the capture molecules are in contact with the PCR solution only during step e) and optionally during step d).

In another embodiment the process of the invention comprises the following steps:
 a) denaturation;
 b) annealing;
 c) elongation;
 d) denaturation;
 e) hybridization; and
 f) detection.

In one embodiment the capture molecules preferably are in contact with the PCR solution only during steps a) and e). In an alternate embodiment the capture molecules are in contact with the PCR solution in all steps, except during step f).

It is desirable that PCR amplification predominantly takes place in solution, and that detection is performed on the formed amplicons along the PCR cycles and does not interfere with the amplification process. It has been found that, for this reason, preferred capture molecules are those comprising a spacer portion and a capture portion. Only the capture portion of the capture molecule is specific of the amplicon. Desirably, the capture molecule is immobilized to a solid support in such a way that the spacer portion is located between the solid support and the capture portion. Preferably, the capture portion of the capture molecule is separated from the surface of the solid support by a spacer portion of at least 6.8 nm.

Conveniently, the spacer portion is a nucleotide sequence, and the nucleotide at the distal end of the spacer portion (that is, the end pointing away from the capture portion) may be used to bind the capture molecule to the solid support. For this purpose the nucleotide at the distal end of the spacer portion may be provided with an amino group, which can form a covalent bond with for example aldehyde groups present at the surface of a pretreated solid support.

The spacer portion should comprise at least 20 nucleotides, preferably at least 40 nucleotides, and more preferably at least 90 nucleotides and is comprise between about 20 and about 120 bases.

Particularly preferred are capture molecules comprising a spacer portion having at least 60% homology, preferably at least 80%, more preferably at least 90%, with the following sequence:

```
                                                 (SEQ ID NO: 2)
5'ATAAAAAAGTGGGTCTTAGAAATAAATTTCGAAGTGCAATAATTATTA

TTCACAACATTTCGATTTTTGCAACTACTTCAGTTCACTCCAAATTA3'
(95 bases).
```

The capture portion of the capture molecule may contain from 10 to 100 nucleotides, preferably from 15 to 40 nucleotides, more preferably from 20 to 30 nucleotides specific of the amplicons produced during the PCR. Preferably, the capture portion of the capture molecule is comprised between 10 and 600 bases, preferably between 20 and 50 bases, more preferably between 15 and 40 bases.

The capture molecule may be immobilized by its 5' end, or by its 3' end.

For multiplexing, capture molecules are immobilized in specifically localized areas of a solid support in the form of a micro-array of at least 4 capture molecules per $cm^2$, preferably at least 20 capture molecules per $cm^2$, more preferably at least 100 capture molecules per $cm^2$. The density of capture molecules on the support is from 20 to 2000 fmoles/$cm^2$.

In a specific embodiment, the capture molecules comprise a capture portion of 10 to 100 nucleotides that is complementary to a specific sequence of the amplicons such that said capture portion defines two non-complementary ends of the amplicons and a spacer portion having at least 20 nucleotides and wherein the two non-complementary ends of the amplicons comprise a spacer end and a non-spacer end, respectively, such that the spacer end is non-complementary to the spacer portion of the capture molecule, and said spacer end exceeds said non-spacer end by at least 50 bases.

In a preferred embodiment, the identification and/or quantification of the biological organism or part of an organism in the sample is performed by monitoring the signal on the different locations of the array with at least two measurements being done per location in at least two cycles of the amplification process. Subsequently the data are processed.

In a specific embodiment, the measurements on the locations are performed at each cycle of the PCR amplification.

In another preferred embodiment, the array comprises at least four different single-stranded capture molecules/$cm^2$ of solid support surface, bound at different locations of the support. Desirably, the four different single-stranded capture molecules are able to specifically bind to four target homologous nucleotide sequences.

In a preferred embodiment, the process of the invention is applied to a sample containing a nucleotide sequence having a homology higher than 30%, preferably greater than 60%, more preferably greater than 80% with at least four other homologous nucleotide sequences that are potentially also present in the sample. In an extreme situation, the nucleotide sequence present in the sample differs by one nucleotide from other homologous nucleotide sequences that are potentially also present in the sample.

In another embodiment, at least two amplicons are detected with at least two capture molecules, and wherein the capture

```
5' AAAGTTGAGTCCATTTGTGATGCTAGAAAAGTTGGAACTTTCTTGAACGTCTCCT    (SEQ ID NO: 1)
ATATGTCATACATGAATAGGTTGATTTTACTGTAC 3' (90 bases).
``` portions of said at least two capture molecules differ by at least 10%, preferably by at least 20%.

Advantageously, the nucleotide molecules to be amplified are homologous nucleotide sequences which are quantified on micro-array during the PCR using consensus primers as described in WO0177372. The same primers are used to amplify all the homologous sequences possibly present in a sample. The amplicons which are labeled with the same fluorescent dye are discriminated on different capture molecules, each one targeting a different homologous sequence. So with only one primer pair and one fluorescent dye, the assay is made multiplex by the use of multiple capture probes present on the micro-array. So the invention preferably uses a consensus primer pair capable of amplifying at least two target sequences having more than 60%, preferably more than 90%, homology, and comprising the use of capture molecules capable of detecting each of the two target sequences.

In one embodiment the number of sequences amplified by the same primer pair is higher than 5 and even higher than 20 and the amplified targets are detected on the array when present in the solution.

In a specific embodiment, the method of the invention comprises the step of extracting from a biological organism or part of an organism a nucleotide sequence specific to that organism.

In another preferred embodiment, PCR cycle comprises labeling nucleotide sequence specific to said organism to form labeled target nucleotide sequences.

In a preferred embodiment, the nucleotide sequence specific to the organism is a DNA nucleotide sequence.

In an alternative embodiment, the nucleotide sequence specific of the organism is an mRNA that is reverse transcribed into cDNA before the PCR.

In another embodiment, a primer pair is used in the at least one PCR cycle, and the same primer pair is used for copying the nucleotide sequence specific to the organism.

In a specific embodiment, the capture molecule is capable of discriminating a target sequence being one strand of the amplicon from another amplicon sequence having less than 85% homology with the target.

In a preferred embodiment, the process of the invention comprises the use of a consensus primer pair capable of amplifying at least two target sequences having more than 60%, preferably more than 90%, homology, and comprising the use of capture molecules capable of detecting each of the two target sequences. In a specific embodiment, the consensus primer pair is capable of amplifying at least 4, preferably at least 10, more preferably at least 20 target sequences having more than 60%, preferably more than 90%, homology, and comprising the use of capture molecules capable of detecting each of the 4, 10 or 20 target sequences.

In another embodiment, at least one PCR cycle comprises the use of a thermostable DNA polymerase enzyme that is active at a concentration in salt comprised between 25 and 300 mM. The preferred salts are: potassium glutamate, potassium chloride and sodium chloride. The polymerase enzyme is preferably a *Thermus aquaticus* DNA polymerase enzyme. Thermostable means which still retains at least 50% of its initial activity after one PCR cycle. Active in salt concentration means an enzyme which shows preferably at least 5% and better at least 20% and still better at least 50% of its activity compared to the activity in solution with salt being lower than 25 mM.

The target nucleotide sequences are preferably labeled by a marker, and the step of detecting the hybridized amplicons comprises the detection of said marker.

In a specific embodiment, the PCR cycle comprises the use of more than one primer pair for the amplification of more than one nucleotide sequence.

In a preferred embodiment, the PCR cycle comprises the use of primers having a sequence that is different from the sequence of the capture molecules.

In another embodiment, the hybridization of an amplicon, specific of an organism, to the capture molecules forms a single spot signal at a predetermined location, whereby the detection of said single spot signal allows the discrimination of the specific amplicon from homologous amplicons from other organisms.

In a preferred embodiment, both the step of detecting the hybridized amplicons to the capture molecules and the PCR cycle are conducted in one chamber. Also the chamber contains a solution containing the specific nucleotide sequence to be amplified, and reagents for nucleotide molecule amplification and an array of immobilized capture molecules.

In another preferred embodiment, the solution contained in the chamber is moved away from the array during the step of detecting the hybridized amplicons. For example, the position of the chamber is moved in order to remove the solution contained in the chamber from the array during the monitoring of the signal on the different locations of the array. In a particular embodiment, this movement comprises turning the chamber upside down.

In a preferred embodiment, the method is performed by monitoring the signal on the different locations of the array with at least five measurements being done per location in at least 5, preferably at least 10 PCR cycles, more preferably at least 20 PCR cycles. Subsequently the data are processed. In a specific embodiment, the process comprises more than 20 PCR cycles, and no measurements are performed during the first 20 PCR cycles.

In a preferred embodiment, the signal is measured at a predetermined time after the start of a PCR cycle and said predetermined time is preferably identical for each location at different PCR cycles.

In another embodiment, the PCR cycle comprises an annealing step, and a signal is measured within 5 min, preferably within 2 min, more preferably within 1 min after the beginning of the annealing step.

In another embodiment, the PCR cycle comprises 3 temperature steps, and a signal is measured at the end of at least one of the 3 temperature steps of the PCR cycle.

In an alternative embodiment, the signal is monitored with time by performing at least two measurements during at least one of the 3 temperature steps of the PCR cycle.

In another embodiment, the PCR amplification is obtained using at least 20 PCR cycles, each comprising the three steps of denaturation, annealing and elongation, whereby each cycle is performed during a time of between 10 sec and 6 min, preferably between 1 and 3 min.

In still another embodiment, the 3 temperature steps are followed by a step of hybridization to the capture molecules. Optionally this hybridization is preceded by a denaturation step.

In a preferred embodiment, the capture molecules are in contact with the PCR solution only during the hybridization step and the detected signal is the result of the accumulation of the amplicons on the capture molecules during the hybridization steps related to different PCR cycles. This embodiment is preferably obtained by the amplification/detection cycle in 6 steps illustrated in FIG. 8b.

In another embodiment, the capture molecules are in contact with the PCR solution during the hybridization step and the denaturation step, and the detected signal is the result of the hybridization of the amplicons on the capture molecules at a given cycle.

In a preferred embodiment, the data are processed by subtracting a first signal, obtained at the denaturation temperature step, from a second signal obtained at the annealing or elongation step, or at the hybridization step. Denaturation step allows the separation of the double strands of the amplicons and the separation of the hybridized strand from the capture molecule.

In another embodiment, a background signal and a signal are measured for each of the different locations and the data are processed by subtracting the background signal from the signal value for each of the different locations. Preferably, the background signal is the local background around the location where the capture molecules are bound. Preferably the quantification of the spots and/or the data analysis are performed as described by de Longueville et al, 2002 (Biochem. Pharmacol. 64, 137-149)

In a preferred embodiment, the quantification of the biological organism or part of an organism in a sample is obtained by comparing the signal value of the different locations with a fixed value.

In another embodiment, the quantification is obtained by comparing the number of PCR cycles necessary to reach a fixed value (CT) with the CT of a reference nucleotide molecule which is preferably a nucleotide molecule amplified in the same solution and detected on the same array as the target nucleotide molecule. Alternatively, the quantification is obtained by comparing the number of PCR cycles necessary to reach a fixed value (CT) with a standard curve wherein the CTs are plotted against standard concentrations.

In another alternative embodiment, the quantification of the biological organism or part of an organism in a sample is obtained by comparing the kinetic constant of the signal of at least two cycles.

The quantification of the organism is preferably performed by quantification of the signal for a genetic element present in the organism. Advantageously, the quantification of a specific organism is performed in terms of copy number in the sample, by comparing signal data of the target specific to the organism to a predetermined number of standard copies added to the analyzed solution.

In another embodiment, the quantification of one organism is performed relative to its family by comparing the amount of a target that is specific to the organism to a target that is specific to the family.

In a particular embodiment, the PCR amplifications of the different targets are performed by PCR having tailed primers, and using second primer(s) identical or complementary to the tail(s) of the tailed primers. In a particular embodiment the tailed primers are used for the amplification of the target(s) and the standards. The PCR solution also contains a second primer(s) identical or complementary to the tail(s) of the tailed primer. The first tailed primer pair, having a common tail, is directed against the specific target(s) and/or the standard and the second primer pair is directed against tail(s) as described by Knut et al. (Nucleic Acids Research, Vol. 31, p. e62, 2003). They also proposed to destroy the tailed primers before amplification with the second primer pair for 5 to 40 cycles.

In a preferred embodiment of this invention, the amplification is performed with the tailed primers and the second primers being both present from the beginning of the amplification, without any destruction of the tailed primers. This method requires the use of an appropriate ratio between the tailed primers and the second primers, the former being at least 5 times lower than the latter, preferably 10 times lower.

In a specific embodiment, the part of the organism to be detected and/or quantified is an expressed gene or mRNA, or its complementary cDNA. The method comprises the step of:

copying the mRNA into a cDNA, amplifying said cDNA or part of it into double-stranded target nucleotide sequences by at least two PCR cycles using a primer pair which is capable of amplifying at least two homologous nucleotide sequences from the same organism;

contacting said target nucleotide sequences with single-stranded capture molecule, said single-stranded capture molecule being covalently bound in a location of an array to an insoluble solid support, and wherein said capture molecules comprise a capture portion of between 10 and 600 bases which is able to specifically bind to said target nucleotide sequence without binding to said at least 4 other homologous nucleotide sequences and detecting specific hybridization of the said target nucleotide sequences to the said capture molecules, wherein the hybridization on capture molecules is combined in one process with the real time PCR for identification and/or quantification of the biological organism or part of an organism in the sample.

In a specific embodiment, the nucleotide sequences are copied by using the primer pair used for the amplification.

In another embodiment, between 1 and 4 nucleotide sequences, preferably between 1 and 20 nucleotide sequences present in the sample are amplified and identified and/or quantified in the same assay.

Advantageously, the method of the present invention may be used for identifying and/or quantifying the presence of several groups, subgroups or sub-subgroups of components or (micro)organisms. Components that are related to each other are amplified using consensus primers. Possible individual genetic sequences (nucleotide and/or amino acid sequences) expected to be potentially present in the sample will bind to the corresponding specific capture molecules, which forms a signal at an expected location. This allows the identification of a target specific to a group, sub-group or sub-subgroup of components or (micro)organisms comprising said components.

For example, the biological components identified by the process of the invention could be different nucleotide sequences specific of the same (micro)organism or specific of different (micro)organisms. Examples of said molecules are homologous nucleotide sequences presenting a high homology such as receptors, HLA molecules, cytochrome P450, etc.

Furthermore, the inventors have discovered that it is possible to drastically simplify the identification or quantification of one or several (micro)organisms or part of it among many other ones present in such biological sample. The identification and/or quantification is obtained by combining a single amplification using common primer pairs and an identification of the possible (micro)organisms or part of it by detecting, quantifying and/or possibly recording upon an array the presence of a single signal resulting uniquely from a specific capture molecule and its corresponding target nucleotide sequence. Subsequently the presence of said detected target nucleotide sequence is correlated to the identity of a nucleotide sequence specific to said (micro)organism(s).

This means that the process of the invention will allow an easy identification/detection of a specific sequence among other homologous sequences, as well as its quantification of a target nucleotide sequence, said target sequence having a nucleotide sequence specific to a particular (micro)organism.

In a preferred embodiment of the present invention, such identification and/or quantification is obtained directly during the amplification cycles without washing, and even in the presence of possible contaminants, by detecting and possibly recording a single spot signal at one specific location where a specific capture molecule was previously bound. The identification is not a result of an analysis of a specific pattern upon the micro-array, as proposed in prior art systems. Therefore, the process of the present invention does not necessarily need a detailed analysis of the pattern by an image processing means and corresponding software as required by the prior art systems.

This invention was made possible by the discovery that target sequences present as a single strand, even with their complementary strand present in the same solution, can be discriminated from other homologous ones upon an array with high sensitivity by using bound capture molecules composed of at least two parts, one being a spacer portion bound by a single and advantageously predetermined (defined) link to the support (preferably a non porous support) and the other part, the capture portion, being a specific nucleotide sequence able to hybridize with the nucleotide target sequence.

This detection is increased when high concentrations of capture molecules are bound to the surface of the solid support.

Furthermore, the detection is greatly increased when the position of the capture portion of the capture molecule relative to the free ends of the hybridized amplicon strand respond to the following feature: the free end of the amplicon located to the spacer portion side of the capture molecule (spacer end) exceeds the free end located in the solution (non-spacer end) by at least 50 bases.

The use of high concentrations, long nucleotide sequences and the specific design of the capture portion of the capture molecules give unexpected characteristic features which allow the present invention. The theory of DNA hybridization proposes that the rate of hybridization between two DNA complementary sequences in solution is proportional to the square root of the DNA length, the smaller one being the limiting factor (Wetmur and Davidson, J. Mol. Biol., Vol. 3, p. 584, 1968). In order to obtain the required specificity, the specific sequences of the capture molecules would have to be small compared to the target. Moreover, the targets are obtained by PCR amplification and are double stranded, so that they reassociate in solution much faster than they hybridize on small sequences fixed on a solid support, where diffusion is low thus reducing even more the rate of reaction. It was unexpected to observe large increase in the yield of hybridization with short specific capture portion sequence. In this invention, the detection is performed during the different cycles of the PCR. This means that the amplicons cannot be cut, because otherwise the amplification would be stopped in subsequent cycles. The results are even more unexpected in that the detection is compatible with the PCR cycles in terms of devices, solutions and physical parameters having to be compatible with two completely different processes: specific amplification and specific detection of full amplicons on a solid support array. Also unexpected is the fact that the reading can be done within 1 to 5 min and even during the annealing step, so that the required amplification time is not, or only slightly, extended over a conventional PCR performed in a reaction tube.

The present invention is also related to the identification of a target nucleotide sequence obtained from a biological (micro)organism or a portion thereof, especially a gene possibly present in a biological sample from at least four other homologous (micro)organisms or a portion thereof. These other (micro)organisms may be present in the same biological sample, and have homologous nucleotide sequences with the target.

Said identification is best obtained by a genetic amplification of said nucleotide sequences (target and homologous sequences) by common primer pairs. It is possible to obtain discrimination between the possible different target amplified nucleotide sequences. This discrimination is advantageously obtained by hybridizing the amplified sequences upon the surface of an array. The array contains capture molecules at given locations that are specific to target nucleotide sequences specific to each (micro)organism possibly present in the biological sample. Specific target nucleotide sequences are detected through the identification and possibly the recording of a signal resulting from the specific binding of this target nucleotide sequence to its corresponding capture molecule at the expected location.

According to the invention, the preferred method for genetic amplification is a PCR using two anti-parallel consensus primers that can recognize all said target homologous nucleotide sequences, but other genetic amplification methods may be used as well.

The (micro)organisms could be present in any biological material or sample, including genetic material obtained from a virus, fungi, bacteria, a plant or animal cell, including the human body. The biological sample can be also any culture medium wherein microorganisms, xenobiotics or pollutants are present, as well as an extract obtained from a plant or an animal (including a human) organ, tissue, cell or biological fluid (blood, serum, urine, sputum, etc).

The process according to the invention can be performed by using a specific identification (diagnostic and/or quantification) kit of a biological organism or part of an organism comprising means and media for performing the method of the invention. Specifically, a preferred kit comprises:

an insoluble solid support surface upon which single-stranded capture molecules are covalently bound, said capture molecules being disposed upon the surface of the solid support according to an array, wherein said array comprises at least 4 different single-stranded capture molecules/cm$^2$ of solid support surface bound at different locations of the support and wherein said capture molecules comprise a capture portion of between 10 and 600 bases which is able to specifically bind to a nucleotide sequence of said organism or part of it, a reaction chamber for performing a genetic amplification together with the identification and/or quantification of amplified nucleotide sequences from said organism or part of it wherein the detection for the presence of any amplified sequences of an organism and the genetic amplification are performed in real time.

In a preferred embodiment the capture molecules bind specifically to at least 4 homologous target sequences being the amplified nucleotide sequences of the organisms or part of it to be detected and/or quantified.

In a preferred embodiment, the capture molecules are able to bind specifically to target sequences having an homology higher than 30%, preferably higher than 60%, more preferably greater than 80%.

In still another preferred embodiment, the capture portion of the capture molecules have a sequence homology lower than 90% and still lower than 80%.

In a preferred embodiment, the array comprises a density of at least 4 and preferably 20 different single-stranded capture molecules per cm$^2$ of solid support surface bound at different locations of the support.

In still another embodiment, the array comprises a density of at least 100 and preferably 300 different single-stranded capture molecules per $cm^2$ of solid support surface, bound at different locations of the support.

In an embodiment, the reaction chamber is composed of two compartments being in fluidic contact with each other.

In yet another embodiment, one compartment is provided with the array with bound capture molecules.

In another embodiment, the diagnostic and/or quantification kit, further comprises: dNTPs, a thermostable DNA polymerase, and buffer. A more complete kit will also contain the primers.

In a preferred embodiment, the diagnostic and/or quantification kit further comprises a nucleotide molecule to be used as an internal standard.

In another embodiment, the support and the reaction chamber are part of a cartridge.

In a preferred embodiment of the kit, the specific sequence of the capture molecule (capture portion), able to hybridize with their corresponding target nucleotide sequence, has a sequence having between 15 and 50 bases or alternatively is separated from the surface of the solid support by a spacer portion of at least 6.8 nm.

In another embodiment of the kit, the spacer portion is a nucleotide sequence of more than 20 bases, preferably more than 40 bases, more preferably more than 90 bases.

In the kit according to the invention, the capture molecules are present on the insoluble solid support in localized areas having a surface area of between 1 $micron^2$ and 75 $mm^2$ and preferably between 0.005 and 0.2 $mm^2$.

The method, kit and device according to the invention are particularly suitable for the identification of a target. Preferably the target is present in a biological (micro)organism, or a part of it. The target may be present in a biological sample where at least 4, 12, 15 or even more homologous sequences are also present. Because of the high homology, said nucleotide sequence can be amplified by common primer(s), so that the identification of the target nucleotide sequence is obtained specifically by the discrimination following its binding with the corresponding capture molecule, which is previously bound at a given location upon the micro-array. The sensitivity can be greater increased when capture molecules are spotted to the solid support surface by a robot, at high density, and according to an array. A preferred embodiment of the invention is to use an amount of capture molecules spotted on the array resulting in the binding of between about 0.01 to about 5 pmoles of sequence equivalent/$cm^2$ of solid support surface.

The kit according to the invention may also incorporate various media or devices for performing the method according to the invention. Said kit can also be included in an automatic apparatus, such as a high throughput screening apparatus, for the detection and/or the quantification of multiple nucleotide sequences present in a biological sample to be analyzed. Said kit or apparatus can be adapted for performing all the steps, or only several specific steps of the method according to the invention.

In the process and the kit according to the invention, the length of the bound capture molecules is preferably comprised between about 30 and about 600 bases, more preferably between about 40 and about 400 bases, and still more preferably between about 40 and about 150 bases. Longer nucleotide sequences can be used if they do not lower the binding yield of the target nucleotide sequences as may result from their adopting a hairpin based secondary structure, or by interacting with each other.

In a preferred embodiment, the specific sequence of the capture molecule, able to hybridize with their corresponding target nucleotide sequence (i.e., the capture portion), is separated from the surface of the solid support by a spacer portion having a length of at least 6.8 nm, corresponding to at least 44 carbon bonds.

The spacer portion is a nucleotide sequence of more than 20 nucleotides, preferably longer than 40 nucleotides, more preferably longer than 90 nucleotides. The nucleotides may comprise a nucleotide derivative, such as PNA.

In a preferred embodiment, the length of the specific sequence of the capture portion is comprised between about 10 and 600 bases, preferably between 20 and 50 bases, more preferably between 15 and 40 bases.

In another preferred embodiment, all capture molecules are polynucleotides of more than 100 bases long.

In another embodiment, the capture molecule is linked to a polymer molecule bound to the solid support. The polymer is preferably a chain of at least 10 atoms, preferably selected from the group consisting of poly-ethyleneglycol, polyaminoacids, polyacrylamide, poly-aminosaccharides, polyglucides, polyamides, polyacrylate, polycarbonate, polyepoxides or poly-ester (possibly branched polymers).

In a particular embodiment, the reaction chamber comprises an inlet and an outlet, which are made water proof during the amplification process.

In another embodiment, the chamber is non symmetrical with a first part having a lower height than the second part. In this embodiment the array is preferably present on the first part of the chamber.

In a particular embodiment, the chamber is made of two parts being in fluidic contact with each other through a microchannel with one of the part having the micro-array. In a specific design the microchannel has a width of no more than 3 mm, preferably less than 1 mm.

In a particular embodiment, the support and/or the chamber material is selected from the group consisting of glass, an electronic device, a silicon support, a plastic support, silica, metal and a mixture thereof, wherein said support is prepared in a prepared in a format selected from the group consisting of slides, discs, gel layers and microbeads.

In still a specific embodiment, the support and/or the chamber material comprise cycloolefin polymer preferably ZEONEX® or ZEONOR® (Zeon Chemicals, Louisville, USA), Topas, Udel, Radel or THV.

If the homology between the sequences to be detected is low (between 30 and 60%), parts of the sequence that are specific to each individual target sequence can be used for the design of specific capture molecules. However, it is more difficult to find a part of the sequence that is sufficiently conserved to provide "consensus" sequences that will amplify or copy all desired sequences. If one pair of consensus primers is not enough to amplify all the homologous sequences, then a mixture of two or more primers pairs is used in order to obtain the desired amplifications. The minimum number of homologous sequences amplified by the same consensus primer is two, but there is no upper limit to this number.

If the sequences show a high degree of homology, higher than 60% and even higher than 90%, then the finding of common sequence for consensus primer is easily obtained, but the choice for specific capture molecules becomes more difficult.

In another preferred embodiment of the invention, the capture molecules are chemically synthesized oligonucleotide sequences shorter than 100 bases (easily performed on programmed automatic synthesizer). Such sequences can bear a functionalized group for covalent attachment to the support.

Longer capture molecules are preferably synthesized by (PCR) amplification of a sequence incorporated into a plasmid containing both the capture portion of the capture molecule and the spacer portion.

In the method according to the invention, the capture portion of the capture molecule is comprised between about 3 and about 60 bases, preferably between about 15 and about 40 bases and more preferably between about 20 and about 30 bases. These bases are preferably assigned as a continuous sequence located at or near one extremity of the capture molecule. This portion is considered the specific sequence for the detection. In a preferred embodiment of the invention, the sequence located between the capture portion and the support is a non specific sequence, preferably the spacer portion.

In another embodiment of the invention, a capture portion comprising between about 3 and about 60 bases, preferably between about 15 and about 40 bases and more preferably between about 20 and about 30 bases, is located on a capture molecule between about 30 and about 600 bases.

The process according to the invention is suitable for the detection and/or the quantification of a target that is made of DNA or RNA, including sequences that are partially or totally homologous upon their total length.

The method according to the invention can be performed even when a target presents a homology (or sequence identity) greater than 30%, greater than 60% and even greater than 80% with other molecules.

In the process according to the invention the capture molecules are advantageously covalently bound (or fixed) to the insoluble solid support, preferably by one of their extremities as described hereafter.

The process according to the invention gives results that allow identification (detection and quantification) with amplicons in solutions at a concentration of lower than about 10 nM, of lower than about 1 nM, preferably of lower than about 0.1 nM and more preferably of lower than about 0.01 nM (=1 fmole/100 microliters).

Another important aspect of this invention is to use very concentrated capture molecules on the surface. If this concentration is too low, the yield of the binding is may be undetectable. Concentrations of capture molecules between about 600 and about 3,000 nM in the spotting solutions are preferred. However, concentrations as low as about 100 nM still give positive results in favourable cases (when the yield of covalent fixation is high or when the target to be detected is single stranded and present in high concentrations). Such low spotting concentrations correspond to a density of capture molecules as low as 20 fmoles per $cm^2$. On the other hand, higher density was only limited in the assays by the concentrations of the capture solutions. Concentrations higher than 3,000 nM give good results.

The amount of a target that "binds" on the spots is small compared to the amount of capture molecules present and is also small compared to the target molecule present in solution.

In one embodiment, the detection is performed on the full length sequence obtained after amplification or copy. When labeling is performed by incorporation of labeled nucleotides, more markers are present on the hybridized target, making the assay sensitive.

After hybridization on the array, the target sequences can be detected by current techniques. In one specific embodiment neither the capture molecules nor the targets are modified with labels and the preferred detection methods are the identification of the target by mass spectrometry now adapted to the arrays (U.S. Pat. No. 5,821,060, which is hereby incorporated by reference herein) or by intercalating agents followed by fluorescent detection (see e.g., Fodor et al., Nature 364, p. 555 (1993), or WO97/27329, which is hereby incorporated by reference herein).

In still another embodiment, the detection of the target sequence being bound on capture molecules is obtained through the labeling of the capture molecules on which the target sequence is bound. Preferably, the extension of the capture molecule free end, preferably the 3' end is performed using detectable nucleotide preferably labeled dNTP. During the temperature step of annealing of a thermal cycle, the primers hybridize with the nucleotide molecule in solution while the amplified target molecule obtained in a previous thermal cycle hybridize in the same time and in the same conditions, on a capture molecule being immobilized in a specifically localized area of a support. During the temperature step of elongation of a thermal cycle, the primers hybridized to the nucleotide molecule are elongated in solution while, the immobilized capture molecules having bound to the target nucleotide molecules are elongated and labeled. Alternate steps of annealing, elongation and denaturation during reaction cycles result in the accumulation of labeled product being partly integrated into its specific capture molecule and which can be detected during or at the end of each of the denaturation step.

In an embodiment, some capture molecules are elongated by the polymerase and some others are in the same time hybridized with the amplified products which accumulate in solution during the thermal cycle. In one embodiment, the capture molecules elongated are detected during the temperature step of denaturation. In another embodiment, the capture molecules elongated and the labeled nucleotide molecules bound on their capture molecule are both detected during the temperature step of annealing and/or elongation.

In a preferred embodiment, the hybridization is favoured over the elongation by using capture probes which are not capable of being elongated. In this case, capture molecules preferably include a base terminator or long stretch of identical bases at their 3' end such as a polyA. Alternatively, the capture molecules are immobilized on the support by their 3' end, the free 5' end being not able to be elongated by the polymerase.

In still another embodiment, the capture molecule bears both a fluorescent quencher or a fluorescent acceptor and a fluorescent donor. The quencher or the fluorescent acceptor is released due to a cut in the capture molecule and the fluorescent donor is detected and or quantified on the support. Preferably cutting the capture molecule results from an enzymatic activity. Preferably the enzyme is specific of double stranded DNA or DNA-RNA and comprises but is not limited to enzymes having the activity of Uracyl DNA glycosylase (UNG), restriction enzyme, 3', 5' exonuclease, 5', 3' exonuclease, RNAseH. Preferably the enzyme is stable at 60° C. and better at 80° C. and still better at 94° C.

In still another embodiment the capture molecule bears a label which is released consecutive to the hybridization of the target to the capture molecule and the fluorescence is the detection signal monitored in the solution along the PCR cycles as described here above in order to perform a real time PCR. In a preferred embodiment the capture molecule bears a fluorescence molecule. In a special embodiment the capture molecule bears both a fluorescent quencher or a fluorescent acceptor and a fluorescent donor. The fluorescent donor is released due to a cut in the capture molecule and the fluorescent donor is detected and or quantified in the solution. Preferably cutting the capture molecule results from an enzymatic activity. Preferably the enzyme is specific of double stranded DNA or DNA-RNA and comprises but is not limited to enzymes having the activity of UNG, restriction enzyme, 3',5' exonuclease, 5',3' exonuclease, RNAseH.

In a specific embodiment, the quenching effect on the capture molecule is obtained by a small distance between the quencher and the fluorescent donor. The capture molecule preferably comprises a hairpin or not as long as the quencher and the fluorescer are maintained at proximity. In a preferred embodiment, the quencher is 1.4 nm diameter gold nanoparticle and the fluorochrome is fluorescein, Rhodamine 6G, Texas red or Cy5. The quencher is preferably located at the free end of the capture probe and the fluorochrome is located at the end or close to the end of the capture molecule which is immobilized on the support. The quencher and the fluorochrome are separated by a uracil base. In the absence of amplicon, the capture probe is quenched. The PCR is performed in the presence of thermostable UNG which hydrolyses the N-glycosilic bond between the deoxyribose sugar and uracil in the DNA capture molecule. Elevated temperature breaks the sugar backbone and uracil is released. When the PCR is in progress, the amplicons hybridize to the capture molecules and the UNG hydrolyzes the uracil which separates the quencher from the fluorescer. The quencher is released and the capture molecule becomes fluorescent.

The invention allows identification of the presence of a polymorphism by using an array having different bounded single stranded capture polynucleotide sequences by the determination of a single signal resulting from the binding between the capture sequence and the target sequence, extending at least one nucleotide of the capture sequence beyond the 3' terminal nucleotide thereof in the 3' 5' direction using the target sequence as a template, said extension is effected in the presence of polymerisation agent and nucleotide precursor wherein at least one nucleotide incorporated into the extended capture sequence is a detectably-modified nucleotide; denaturing the duplex to free the target sequence from the polynucleotide capture nucleotide sequence, carry out step one or more times and detecting the presence of a signal associated with the detectable modified nucleotide in the extended capture nucleotide sequence at the reaction zone to effect said determination. The process is repeated along the PCR cycles to obtain a signal detectable on the array.

In one embodiment, the process according to the invention comprises the use of other bound capture molecules, which have the same characteristics as the previous ones and are used to identify a target from another group of homologous sequences. These homologous sequences are preferably amplified by common primer(s).

In the microbiological field, amplification is preferably performed using consensus primer(s) specific for each family, or genus, of micro-organisms and then some or all the species of these various families are then identified on an array by using capture molecules according to the invention. Detection of other sequences can be advantageously performed on the same array (e.g., by allowing a hybridization with a standard nucleotide sequence used for the quantification, with consensus capture molecules for the same or different microorganism strains, with a sequence allowing a detection of a possible antibiotic resistance gene by micro-organisms or for positive or negative control of hybridization). Said other capture molecules may have a specific sequence longer than 10 to 60 bases and a total length as high as 600 bases, and are also bound to the insoluble solid support (preferably in the array made with the other bound capture molecules related to the invention). A long capture molecule may also be present on the array as consensus capture molecule for hybridization with all sequences of the microorganisms from the same family or genus, thus giving the information on the presence or not of a microorganism of such family, genus in the biological sample.

In a specific embodiment, the same array also bears capture molecules specific to a bacterial group, and as specific application to Gram-positive or Gram-negative strains, or even all the bacteria.

Another application is the detection of homologous genes from a consensus protein of the same species, such as various cytochromes P450, by specific capture molecules with or without the presence of a consensus capture molecule for all the cytochromes P450 possibly present in a biological sample. Such detection is performed at the gene level by reverse transcription into cDNA.

The solid support according to the invention is preferably made with materials selected from the group consisting of glasses, electronic devices, silicon supports, plastic supports material, silica, metal or a mixture thereof in format such as slides, compact discs, gel layers, and microbeads. Advantageously, said solid support is a single glass slide which may comprise additional means (barcodes, markers, etc.) or media for improving the method according to the invention. One of the preferred support comprises polymer having chemical and thermal stability, low fluorescence and optical stability, preferably cyclo-olefin polymer such as ZEONEX® or ZEONOR® (Zeon Chemicals, Louisville, USA), or but not limited to, Topas, Udel, Radel or THV.

The amplification step used in the method according to the invention is advantageously obtained by well known amplification protocols, preferably selected from the group consisting of PCR, RT-PCR, LCR, CPT, NASBA, ICR or Avalanche DNA techniques.

Advantageously, the target nucleotide sequence to be identified is labeled prior to its hybridization with the single stranded capture molecules. Said labeling (with known techniques to the person skilled in the art) is preferably also obtained upon the amplified sequence prior to the denaturation (if the method includes an amplification step).

Advantageously, the length of the target nucleotide sequence is selected as being of a limited length, preferably between 50 and 2000 bases, more preferably between 200 and 800 bases. This preferred requirement depends on the possibility to find consensus primers to amplify the required sequences possibly present in the sample. Too long a target nucleotide sequence may reallocate faster and adopt secondary structures, which may inhibit the fixation on the capture molecules.

The detection of homologous expressed genes is obtained by first carrying out a reverse transcription of the mRNA by a consensus primer, the preferred one being the polydT. In one embodiment, the reverse transcribed cDNA is then amplified by consensus primers as described herein.

According to a further aspect of the present invention, the process according to the invention is advantageously used for the identification of different *Staphylococcus* species or variants, preferably the *S. aureus*, the *S. epidermidis*, the *S. saprophyticus*, the *S. hominis* or the *S. haemolyticus*. For homologous organs of this type, which may be present together or separately in the biological sample, identification is obtained by detecting the genetic variants of the FemA gene in said different species, preferably by using a common location in the FemA genetic sequence. In another aspect of the invention, 16 *Staphylococcus* species could be detected after amplification by the same primers and identification on the array.

A further aspect of the invention is the detection of *Mycobacteria* species, the *M. tuberculosis* and other species, preferably the *M. avium, M. gastrii, M. gordonae, M. intracellulare, M. leprae, M. kansasi, M. malmoense, M. marinum, M. scrofulaceum, M. simiae, M. szulgai, M. xenopi, M. ulcerans.*

In a further application of the invention, one array can specifically detect amplified sequences from several bacterial species belonging to the same genus or from several genera like *Staphylococcus, Streptococcus, Enterococcus, Haemophilus* or different bacterial species and genera belonging to the Gram-positive bacteria and/or to the Gram-negative bacteria.

Preferably, the primer(s) and the specific portions of gyrase (sub-unit A) sequences are used for obtaining amplified products. These primers have been selected as consensus primers for the amplification of the gyrase genes of all of the bacteria tested and they probably will amplify the gyrase from many other possible bacteria species and genus and families.

The invention is particularly suitable for detection of bacteria belonging to at least two of the following genus families: *Staphylococcus, Enterococcus, Streptococcus, Haemolyticus, Pseudomonas, Campylobacter, Enterobacter, Neisseria, Proteus, Salmonella, Simonsiella, Riemerella, Escherichia, Neisseria, Meningococcus, Moraxella, Kingella, Chromobacterium, Branhamella.*

The same application was developed for the G Protein Coupled Receptors (GPCR). These receptors bind all sorts of ligands and are responsible for the signal transduction to the cytoplasm, and very often to the nucleus by modulating the activity of the transcriptional factors. Consensus primers are formed for the various subtypes of GPCR for dopamine and for serotonin and histamine. The same is possible for the histamine and other ligands. The detection of the various HLA types is also one of the applications of the invention. HLA are homologous sequences which differ from one individual to the other. The determination of the HLA type is especially useful in tissue transplantation in order to determine the degree of compatibility between the donor and the recipient. It is also a useful parameter for immunization. Given the large number of subtypes and the close relationship between the homologous sequences it was not always possible to perfectly discriminate one sequence among all the other ones and for some of them there were one or two cross-reactions. In this case, a second capture molecule complementary to another location of the amplified sequence was added on the array, in order to make the identification absolute.

The detection of polymorphism sequences (which can be considered as homologous even if differing by only one base) can be made also by the method according to the invention. Discrimination of the Cytochrome P450 forms is one particular application of the invention because the presence of certain isoforms modifies the metabolism of some drugs. The invention was found particularly useful for discriminating between the isoforms of Cytochrome P450 2D6, 2C9 and 2C19. More generally the invention is particularly well adapted for genotyping an organism or for the discrimination of sequences differing by one base mutation or deletion called Single Nucleotide Polymorphism (SNP). A unique feature of the invention is that the hybridization step is performed directly on the amplified sequences, without the necessity to copy into RNA and to cut them into pieces.

Furthermore, one array can specifically detect amplified sequences from several animal species and genera belonging to several families like Galinacea, Leporidae, Suidae and Bovidae.

One array can specifically detect amplified-sequences from several fishes species, such as *G. morhua, G. macrocephalus, P. flesus, M. merluccius, O. mykiss, P. platessa, P. virens, S. salar, S. pilchardus, A. thazard, T. alalunga, T. obesus, R. hippoglossoides, S. trutta, S. sarda, T. thynnus, S. scombrus* belonging to several genera such as *Auxis, Sarda, Scomber, Thunnus, Oncorhynch, Salmo, Merluccius, Pleuronectes, Platichtlys, Reinhardtius, Pollachius, Gadus, Sardina*, from several families such as Scombridae, Salmonidae, Merluccidae, Pleuronectidae, Gadidae and Clupeidae. Other homologous sequences allow the determination of plant species and genera, such as potato, tomato, oryza, zea, soy, wheat, barley, bean, carrot, belonging to several families.

According to a further aspect of the present invention, the process according to the invention is advantageously used for the identification of the origin of meat.

Preferably, the primer(s) and the specific portions of cytochrome b sequences are used for obtaining amplified products. These primers have been selected as consensus primers for the amplification of the cytochrome B genes of all of animals tested and they probably will amplify the cytochrome B from many other animal species, genera, and families.

According to a further aspect of the present invention, the process according to the invention is advantageously used for the identification of the origin of fishes.

According to a further aspect of the present invention, the process according to the invention is advantageously used for the identification of the origin of plants.

Preferably, the primer(s) and the specific portions of sucrose synthase sequences used for obtaining amplified products are the ones described hereafter in the examples. These primers have been selected as consensus primers for the amplification of the sucrose synthase genes of all plants tested, and they probably will amplify the sucrose synthase from many other plant species, genera, and families.

According to a further aspect of the present invention, the process according to the invention is advantageously used for the identification of Genetically Modified Organisms (GMOs). The GMOs are produced by insertion into the genome of an organism of one or several external genes together with other regulating or construction sequences.

Preferably, the primer(s) and the specific portions of said sucrose synthase sequences used for obtaining amplified products are the ones described hereafter in the examples. These primers have been selected as consensus primers.

According to a further aspect of the present invention, the process according to the invention is advantageously used for the identification of organisms or part of it as provided in the examples cited here above and also the ones presented in the examples 1 to 2.

Another aspect of the present invention is related to any part of biochips or micro-array comprising said above described sequences (especially the specific capture molecules described in the examples), as well as a general screening method for the identification of a target sequence specific to said (micro)organisms of family type discriminated from homologous sequences upon any type of micro-arrays or biochips by any method.

Hybridized targets are detected on the array by a series of method described but not limited to the ones presented here under as long as they are compatible with the constraints given by the PCR. A non-labeled method has been proposed to be applicable on array and is based on identification of the target by mass spectrometry adapted to arrays (U.S. Pat. No. 5,821,060, which is hereby incorporated by reference herein in its entirety).

The label-associated detection methods are numerous. A review of the different labeling molecules is given in WO 97/27317, which is hereby incorporated by reference herein in its entirety. They are obtained using either already labeled primer, or by enzymatic incorporation of labeled nucleotides during the copy or amplification step or by intercalating agents followed by fluorescent detection (WO 97/27329, which is hereby incorporated by reference herein in its entirety).

The most frequently used labels are fluorochromes like Cy3, Cy5 and Cy7 suitable for analyzing an array by using array scanners (General Scanning, Genetic Microsystem). The resulting signal of target fixation on the array can be detected using fluorescent, colorimetric, diffusion, electroluminescent, bio- or chemiluminescent, magnetic, electric-like impedometric or voltametric (see e.g., U.S. Pat. No. 5,312,527, which is hereby incorporated by reference herein in its entirety), or radioactive detection.

The preferred labels are fluorochromes which are detected with high sensitivity with fluorescent detector. Fluorochromes include but are not limited to cyanine dyes (Cy3, Cy5 and Cy7) suitable for analyzing an array by using commercially available array scanners (as available from, for example, General Scanning, Genetic Microsystem). Preferably, the excitation wavelength for Cy3 is between about 540 and 558 nm with a peak at 550 nm, and the emission wavelength is between about 562 and 580 nm with a peak at 570 nm. Preferably, the excitation wavelength for Cy5 is between about 639 and 659 nm with a peak at 649 nm, and the emission wavelength is between about 665 and 685 nm with a peak at 670 nm. Preferably, the excitation wavelength for Cy7 is between about 733 and 753 nm with a peak at 743 nm, and the emission wavelength is between about 757 and 777 nm with a peak at 767 nm.

In a preferred embodiment of the invention, the detection of the fluorescence signal related to the presence of the amplicons on the capture molecule takes party of a signal increase on the array as compared to the fluorescence in solution. In a particular embodiment the difference of the detection of the fluorochrome present on the array is based on the difference in the anisotropy of the fluorochrome being associated with a bound molecule hybridized on the capture molecule as a DNA double helix compared to the free moving molecule in solution. The anisotropy depends on the mobility and the lifetime of the fluorochromes to the detected. The method of assay for the anisotropy on array is now available from Blueshift Biotechnologies Inc., 238 East Caribbean Drive, Sunnyvale, Calif. 94089 (http://www.blueshiftbiotech.com/dynamicfl.html).

In a particular embodiment, the detection of fluorophore molecule is obtained preferably in a time-resolved manner. Fluorescent molecules have a fluorescent lifetime associated with the emission process. Typically lifetimes for small fluorophore such as fluorescein and rhodamine are in the 2-10 nanosecond range. Time-resolved fluorescence (TRF) assays use a long-lived (>1000 ns) fluorophores to discriminate assay signal from short-lived interference such as autofluorescence of the matrix or fluorescent samples which almost always have lifetimes much less than 10 ns. Lifetime is preferably modulated by the presence in the vicinity of another fluorophore or a quencher with which a resonant energy transfer occurs. Instruments for TRF simply delay the measurement of the emission until after the short-lived fluorescence has died out and the long-lived reporter fluorescence still persists. Fluorescence lifetime can be determined in two fundamental ways. The time domain technique uses very short pulses (picosecond) of excitation and then monitors the emission in real time over the nanosecond lifetime. Fitting the decay curve to an exponential yields the lifetime. The frequency domain technique modulates the excitation at megahertz frequencies and then watches the emission intensity fluctuate in response. The phase delay and amplitude modulation can then be used to determine lifetime. The frequency technique for fast and economical lifetime imaging is now available from Blueshift Biotechnologies Inc.

In a preferred embodiment of the invention, the step of detecting the hybridized amplicons takes party of a fluorescence signal of the amplicons lower in solution than on the hybridized capture molecule.

In a particular embodiment, the lower fluorescent signal of the amplicons in solution compared to the hybridized amplicons is obtained by quenching of the fluorochrome. A primer is labeled with a fluorochrome which is fluorescent when free in the solution and is quenched when incorporated into the amplicons. The fluorescence quenching is preferably obtained by using a quencher such but not limited to Dabcyl incorporated in the second non fluorescent amplicon strand. One specific embodiment used the PLEXOR™ Technology (Promega). This technology takes advantage of the highly specific interaction between two modified nucleotides: isoguanine (iso-dG) and 5'-methylisocytosine (iso-dC). In the real time PCR reaction, one primer is synthesized with an iso-dC residue and a fluorochrome at the 5' end. The second primer is unlabeled. Iso-dGTP nucleotides, modified to include Dabcyl as a quencher, are included in the reaction mix. During the amplification only Dabcyl-iso-dGTP is incorporated at the position complementary to the iso-dC residue and as a result of the close proximity between the two residues, the fluorescence is quenched. The hybridization of the amplicon strand carrying the fluorochrome on the capture molecule would restore the fluorescence emission.

In an alternative embodiment, the lower signal of the amplicons in solution is obtained by a difference in the optimal wavelength of fluorescence excitation between the amplicons present in solution and immobilized on the capture molecule. In still another embodiment, the lower signal of the amplicons in solution is obtained by a difference in the optimal wavelength of fluorescence emission between the amplicons present in solution and immobilized on the capture molecule.

Preferably, the difference in the wavelength of fluorescence emission is obtained by fluorescence resonance energy transfer (FRET). In one specific embodiment, a primer is labeled with a fluorochrome (F1) having a given optimal fluorescent emission wavelength and serving as donor that is fluorescent when excited at its excitation wavelength in the solution. The incorporation of the primer into the amplicon at proximity of a fluorochrome acceptor (F2) would result in an optimal fluorescence emission wavelength different from the fluorochrome F1. By detecting the fluorescence emission at the wavelength corresponding to the optimal emission of F1, the signal will be optimal for the hybridized amplicons and will be lower for the amplicons present in the solution. Particularly, the primer is synthesized with an iso-dC residue and a fluorochrome donor (i.e. TAMRA) at the 5'end and the solution contains Iso-dGTP nucleotides, modified to include a fluorochrome acceptor (i.e. Cy5). During the PCR, the amplicons are formed with the two fluorochromes being at close proximity as explained previously for the Plexor™ Technology (Promega). Detection is then performed using an excitation/emission wavelength optimal for the donor. As a result of the close proximity between the donor and the acceptor, the detected fluorescence is decreased in solution. The hybridization of the amplicon strand carrying the donor on the capture molecule would restore the optimal fluorescence emission.

The above described methods allow a better discrimination between the amplicons present in solution and hybridized on the capture molecule.

In another preferred embodiment, the excitation of the fluorophore molecule is obtained preferably on the fluorophore present on target bound to the capture molecule rather that on the fluorophore present in the solution. In a preferred method, the excitation is obtained by a laser beam which is focussed on the surface of the array. Scanner method with a focusing of the laser beam used a confocal scanning method including a pin hole. Many such scanners are commercially available such as the PROSCANARRAY® line of scanners from PerkinElmer® Life, the Affymetrix 428 scanner, the Virtek Vision Chipreader line, etc. Some fluorescence laser based detection is now available for multiwell formats as for example the Safir from Tecan (Tecan Trading AG, Männedorf, Switzerland; www.tecan.com). They could be adapted for the present invention.

In another embodiment the excitation of the fluorochrome is obtained by illumination the sides of the array substrate so as to give the excitation to the molecules close to the surface. In a preferred embodiment, the device for detecting a signal comprises a light source illuminating the sides of the insoluble solid support. The light source is preferably a non collimated laser source or a light emitting diode by a pair of optical fiber bundles as proposed by Aurora Photonics Inc. (26791 West Lakeview, Lake Barrington, USA; info@auroraphotonics.com).

In still another embodiment the fluorescence excitation is provided through fiber optics on which the capture molecules are fixed. U.S. Pat. No. 6,503,711 provides a system based on the use of an index of refraction of the immobilized layer equal to or greater than the refractive index of the interaction surface of the optical element such that direct excitation of the fluorophore in the immobilization layer results in the detection of the target nucleic acid.

Some fluorescent labels may be of particular interest, such as nanocrystalline particles having fluorescent properties. The most common ones are the Quantum dots (Han et al., Nature Biotechnology, Vol. 19, p. 631, 2001). They are fluorescent and do not bleach with time or with illumination. Their stability makes them particularly suitable for the use in continuous reading, as proposed in this invention. Also, they contain metals that confer to these particles specific properties, so that other methods than fluorescence can be used to monitor their attachment to the capture molecules. Thermal heating of these particles is one of the parameters that may be monitored with time. The fact that the metal absorbs the energy of a light beam, preferably a laser beam, and induces heating of the particle, has been used as a basis for the detection of low density gold particles on a support, and even single particles are detected (Boyer et al., Science, Vol. 297, p. 1160, 2002). The method is called Photothermal Interference contrast.

Direct method for detection of the binding of the target molecules on capture molecule of the micro-array is the chemical cartography based on optical process of non-linear generation frequency spectroscopy (GFS) (L. Dreesen et al., Chem Phys Chem, Vol. 5, p. 1719, 2004). This technology allows the imaging in real time of the vibrational properties of surfaces and interfaces with a submicron spatial resolution. The measurement is obtained by mixing at the surface of a substrate two laser beams, one having a fixed frequency in the visible (green) and the other having a variable frequency in infrared. The vibrational signature at the interface is obtained by measuring the light emitted by the sample in function of the frequency of the infrared laser beam. This method avoids labeling the target to be detected and so it represents a particular embodiment.

Another technology for the direct measurement of nanoparticles is Rayleigh scattering. This method is based on the use of a light beam adapted in order to obtain an oscillation of the electrons in a metal particle so that an electromagnetic radiation is obtain from the particle, which can be detected. (Stimpson et al., Proc. Natl. Acad. Sci. USA, Vol. 100, p. 11350, 2003) (real-time detection of DNA hybridization and melting on oligonucleotide arrays by using optical wave guides) However until now the method is lacking the necessary sensitivity for application on biological samples.

Alternatively, Raman scattering and surface plasmon resonance may be applied in the present invention, which techniques have been extensively used for the detection of antibody/antigen binding, but are also well suited for the multiparametric measurement of the arrays and for the required sensitivity on biological samples. (Thiel et al., Analytical Chemistry, Vol. 69, p. 4948, 1997).

In another embodiment, quartz crystal microbalances may be applied, which are now sensitive enough that they can measure changes of mass less than one nanogram (cf. Caruso et al., Analytical Chemistry, Vol. 69, p. 2043, 1997). This is one proposal for micro-array detection in real-time.

Cantilevers are another option for the detection of DNA on micro-arrays. (McKendry et al., Proc. Natl. Acad. Sci. USA, Vol. 99, p. 9783, 2002).

Also, another technology is the electrical detection of nanoparticles, which takes into account their metal properties. Electrochemical detection was first applied, but with low sensitivity. A more advanced and more sensitive method is the detection by differential pulse voltametry (Ozsoz et al., Analytical Chemistry, Vol. 75, p. 2181, 2003). The resistivity and the capacitance properties of the metal are among the best properties to be detected on electronic chips. The presence of a metal between two electrodes induces a change in the electric properties of the chips or the electrodes including change of resistivity or conductance and/or of capacitance and/or impedance. The detection of the DNA or proteins is then observed when the capture molecules are present on one of the electrodes (Moreno-Hagelsieb et al., Sensors and Actuators B-Chemical, Vol. 98, p. 269, 2004). The capacitance assay of gold labeled DNA has been described by Guiducci et al. (Biosens Bioelectron, Vol. 19, p. 781, 2004). Since electronic chips can be made to comprise several plots, different targets may be detected on different plots and the change in the resistivity or in the capacitance may be recorded. One promising method is the use of interdigitated electrodes which allows compatibility between the array pattern and the location on the electrodes. Although these methods have not yet been able to produce the reliable and sensitive detections required by biological samples, some of them will succeed to fulfil the requirements for real-time detection (see review of the detection methods for the nanoparticles by Foultier et al., IEE Proc. Nanobiotechnol., Vol. 152, p. 3, 2005). Another method for the detection of the particles is to count them according to their location on the array by optical method such as described by Blab et al. (Biophysical J., Vol. 90, p. L13, 2006). The method relies on Laser Induced Scattering around a NanoAbsorber (LISNA). It provides direct counting of individual nanoparticles on each spot of the array.

In a preferred embodiment, the signal monitored on the different locations of the array is selected from the group consisting of: colorimetry, fluorescence, time-resolved fluorescence, photothermal interference contrast, Rayleigh scattering, Raman scattering, surface plasmon resonance, change of mass, quartz crystal microbalances, cantilevers, differential pulse voltametry, chemical cartography by non linear generation frequency spectroscopy, optical change, resistivity, capacitance, anisotropy, refractive index and/or counting nanoparticles.

Quantification has to take into account not only the hybridization yield and detection scale on the array (which is identical for target and reference sequences) but also the extraction, the amplification (or copying) and the labeling steps.

The method according to the invention may also comprise means for obtaining a quantification of target nucleotide sequences by using a standard nucleotide sequence (external or internal standard) added at a known concentration. A capture molecule is also present on the array, so as to fix the standard in the same conditions as said target (possibly after amplification or copying); the method comprises the step of quantification of a signal resulting from the formation of a double stranded nucleotide sequence formed by complementary base pairing between the capture molecules and the standard and the step of a correlation analysis of the signal resulting from the formation of said double stranded nucleotide sequence with the signal resulting from the double stranded nucleotide sequence formed by complementary base pairing between capture molecule(s) and the target, in order to quantify the presence of the original nucleotide sequence to be detected and/or quantified in the biological sample.

Advantageously the standard is added to the initial biological sample, or after the extraction step, and is amplified or copied with the same primers and/or has a length and a GC content identical to, or differing by no more than 20% from, the target. More preferably, the standard can be designed as a competitive internal standard having the characteristics of the internal standard found in the document WO 98/11253, which is hereby incorporated by reference herein in its entirety. Said internal standard has a part of its sequence common to the target, and a specific part that is different. It also has at or near its two ends sequences that are complementary to the two primers used for amplification or copy of the target and similar GC content (WO 98/11253, which is hereby incorporated by reference herein in its entirety). In a preferred embodiment of this invention, the term "common part of the standard and the target" means a nucleotide sequence that is homologous to all target amplified by the same primers (i.e. which belong to the same family of organisms to be quantified).

Preferably, the hybridization yield of the standard through this specific sequence is identical to, or differ no more than 20% from, the hybridization yield of the target sequence, and quantification is obtained as described in WO 98/11253, which is hereby incorporated by reference herein in its entirety.

Said standard nucleotide sequence, external and/or internal standard, is also advantageously included in the kit according to the invention, possibly with all the media and means necessary for performing the different steps according to the invention (hybridization and culture media, polymerase and other enzymes, standard sequence(s), labeling molecule(s), etc.).

Advantageously, the solid support or the biochips also contain spots with various concentrations (e.g., 4) of the labeled capture molecules. These labeled capture molecules are spotted from known solution concentrations, and their signals allow the conversion of the results of hybridization into absolute amounts. They also allow testing the reproducibility of the detection.

The solid support of the biochips can be inserted in a support connected to another chamber and automatic machine through the control of liquid solution based upon the use of microfluidic technology. By being inserted into such a microlaboratory system, it can be incubated, heated, washed and labeled by automates, even for preliminary steps (like extraction of DNA, genetic amplification steps) or the identification and discrimination steps (labeling and detection). All these steps can be performed upon the same solid support.

The present invention is also related to a method for identifying homologous sequences (and the groups to which they belong, and eventually the organisms and their groups) possibly present in a biological sample by assay of their genetic material in an array-type format. The method is well adapted for determination of organisms belonging to several groups, being themselves members of a super-group. The method is for example well adapted for a biological determination and/or classification of animals, plants, fungi or micro-organisms.

The method involves the use of multiple capture molecules present as arrays, the capture of the corresponding target sequences and their analysis, and possibly their quantification. The method also allows the identification of these organisms and their groups by characterization of the positive area of the arrays bearing the required capture molecules. One particular specification of the invention is the fact that a positive hybridization, resulting in a spot on the array, gives the necessary information for the identification of the sequence or the organism or the group or sub-group from which it belongs.

It also provides a method for sequential analysis of the presence of any researched organisms during the genetic amplification, followed by the detection of amplicons on the array and identification of the corresponding organisms or groups thereafter.

Furthermore, the inventors have discovered that is possible to obtain, by the method of the invention, a very quick and easy identification of such multiple sequences belonging to several groups or sub-groups or sub-sub-groups of sequences being homologous to each others, until possible individual sequences, by combining a single nucleotide amplification, preferably by PCR, using common primer pair(s) together with an identification of the organisms at different level(s) by detecting and possibly recording upon an array having at least 5 different bound single stranded capture molecules/cm$^2$ of solid support surface, the presence of a single signal resulting from the binding between a capture sequence and its (or their) corresponding target sequence(s), and thereafter correlating the presence of said detected target sequences to the identification of a specific genetic sequence among the other ones. The method is especially well adapted for the identification of organism species, genus and family through the analysis of a given part of their genome or gene expressed, these sequences being homologous to each other in the different organisms.

A single signal means a signal that by itself is sufficient to identify one or more target nucleotide sequence(s) to which it is designed, and therefore to give (if necessary) an unambiguous response for the presence or not of the organisms or groups of organisms present in the sample, or the organisms or group of organisms from which said sample has been obtained.

The method according to the invention allows easy identification/detection of a specific nucleotide sequence among other possible amplified nucleotide sequences, and optionally their quantification (characterization of the number of copies or presence of said organisms in a biological sample) of target sequences, said target nucleotide sequences having a nucleotide sequence specific to said organisms or groups of organisms.

The array may contain capture molecules from several organism genera and, from several species within a genus. The capture molecules may detect the genus, the species and also the family(ies) to which these genera belong. The capture molecules may also detect the sub-species and even the individual organisms of one or several species. Individual organisms of a given species are considered as having very homologous sequences, differing mainly by single bases within some of their DNA sequences or genes. Homology is important for getting consensus primers, and a single base change is sufficient to obtain discrimination between two target amplicons. If not complete, the discrimination can be confirmed by the use of second capture molecules present upon the array and able to bind the same amplicon at different sequence locations.

Said identification is obtained firstly by a genetic amplification of said nucleotide sequences (target sequences) by common primer pair followed (after washing) by discrimination between the possible different targets amplified according to the above described method.

The amplified sequences may belong to the same gene, may be part of the same DNA locus, and are homologous to each others.

The method also applies to the identification and possibly characterization of nucleotide sequences as such, independently from the organism. Genes or DNA sequences can be classified in groups and sub-groups and sub-sub-groups according to their sequence homology. Bioinformatic programs exist for sequence alignment and comparison (such as Clustal, Intelligenetics, Mountain View, Calif., or GAP, BESTFIT, FASTA and TFASTA in the Wisconsin Genetics Software Package, Genetics computer Group Madison, Wis., U.S.A. or Boxshade). A classification can be made according to the percentage of homology and alignment of the sequences. An interest in detection and identification of the sequences from a given family in a given organism, tissue or cell is for example the possibility to detect the effect of any given molecules, biological or pathological conditions (by proteomics, functional genomics, etc.) upon both the overall and the specific genes of one or several families.

The inventors also found that sensitivity of the assay was increased by using a high density of capture molecules fixed on the support, preferably higher than about 100 fmoles/cm$^2$ of solid support surface.

The capture molecules specific for the determination of a group of organisms are designed in a way as to be able to specifically capture the different sequences belonging to the various groups. These capture molecules are called consensus for this group of organisms. The consensus capture molecules may contain specific sequences that are longer than the specific capture molecules of the different members of the group. In one embodiment, the present invention allows the use of the same stringency conditions, mainly determined by the salt concentration and the temperature and the rate of reaction, for capturing different sequences from the various groups.

These capture molecules are consensus sequences, (i.e. the sequences containing at each of its location the base that is the most present in the different sequences of the members of the group when aligned). In another embodiment the consensus capture molecule has the length of the amplified sequences.

According to the invention, organisms are identified as such by their specific polymorphism. Single base substitution in a particular location of genome is the characteristic of an individual organism among others of the same species. The method for identification of the polymorphism is part of the invention with direct hybridization of the amplified sequences on the capture molecules of the array and detection of the fixed target sequence.

The invention also allows identification of the presence of a polymorphism by using an array having at least five different bounded single stranded capture polynucleotide sequence/cm$^2$ of solid support surface, the determination of a single signal resulting from the binding between the capture sequence and the target sequence, extending at least one polynucleotide primer of the hybrid beyond the 3' terminal nucleotide thereof in the 3' to 5' direction using the polynucleotide sequence as a template, said extension is effected in the presence of polymerization agent and nucleotide precursor wherein at least one nucleotide incorporated into the extended primer molecule is a detectably-modified nucleotide.

The arrays may be present in the surface of multiwells and multiwell plate detectors may be used for the reading of the results.

In a particular embodiment the array bears, in separated areas, several identical capture molecules differing only by one nucleotide located at the same place in the capture molecule, the last free end is the interrogation base. The array is then able to identify the presence of any of the 4 bases present at a given location of the sequence. Such an array is especially useful when detecting polymorphism in homozygote or heterozygote organisms, or when the polymorphism is not known.

In the process according to the invention, the capture portion(s) (or part(s)) of the capture molecules complementary to the target sequence is composed of at least two families. The first one comprises between about 5 and about 60 bases, preferably between about 15 and about 40 bases and more preferably between about 20 and about 30 bases. In the second capture family, the capture portion of the capture molecule sequences are comprised between about 10 and 1000 bases and preferably between 100 and 600 bases. These bases are preferably assigned as a continuous sequence located at or near the extremity of the capture molecule. This capture portion is considered as the specific sequence for the detection. In a preferred form of the invention, the sequence located between the capture portion and the support surface is a non-specific sequence or capture portion.

In another preferred embodiment of the invention, a first family of capture molecules detect the members of a group, while a second family of capture molecules detect the group as such. However, both families of capture molecules can be polynucleotides.

The consensus primers can be chosen in order to amplify different sequences and groups of sequences. The same pair of primers amplifies several groups of sequences that are different for the different groups of homologous sequences, each one being associated with one or several groups of organism. The pair of consensus primers may be associated with group identification and/or for species identification on the array.

In a specific embodiment a second or third or even more primers are added for the amplification step in order to possibly amplify other sequences, related or not to one particular group, and useful to be detected in the sample. Viruses susceptible to be present in a clinical sample together with bacteria are one example where such aspect of the invention is particularly useful like the combination of virus detection.

In another specific embodiment, two pairs of (possibly consensus) primers are used for the amplification, one for amplification of sequences of the Gram-positive and the other one for the Gram-negative bacteria. The amplified sequences are specific to either the Gram-positive or the Gram-negative bacteria, and are detected thereafter on the array as specific bacteria species or/and genus and/or family). Each of the two primers pair amplifies various sequences specific to one or several families that are then detected as specific species or/and genus, families on the array. The same array preferably bears capture nucleotides sequences specific to bacterial families or genus.

In one preferred embodiment of the invention, the detection of the presence of any member of the groups are first detected during the PCR using method like the real time PCR and the amplicons are thereafter used for identification on the array.

The fluorescent signal of the amplification solution is registered, and if it crosses a threshold, the solution is processed for hybridization on capture molecules of the array. In a preferred embodiment, a solid support bearing the array is added in the amplification chamber and in the hybridization processes. In another preferred embodiment the hybridization is performed on the surface of the same chamber as the PCR. Chambers, preferably closed chambers, are of any size, format and material as compatible with arrays. The chambers may be in polymers such as polycarbonate, polypropylene, or glass such as capillaries or a mixed of materials. Polyacrylate based surfaces are particularly useful since they are transparent to light and allow covalent binding of capture molecules necessary for the arrays. The free end, of the capture molecule has preferably either a 5' or 3'-OH or phosphate group modified in order to avoid elongation. Preferably, the capture portion of the capture molecule has a melting temperature smaller than the primers used for the amplification in order to avoid hybridization during the PCR cycles. Also the hybridization is preferably performed at a given temperature using the heating and control system of the amplification cycler. Preferably, a control process is provided on the amplification cycler to continue or not the detection on the array after the amplification steps.

One embodiment of the invention is to combine in one process the real time PCR together with the hybridization on capture probes for identification of the target molecules or organisms. In a preferred embodiment the process is performed in the same chamber and with the same machine device. For example, one may combine in one process the real time PCR together with the hybridization on capture molecules for identification of the target molecules or organisms in the same chamber and with the same device.

In one embodiment, the different parts of the diagnostic and/or quantification apparatus necessary for making the PCR amplification and the detection on the array are integrated into the same apparatus in order to detect the target nucleotide molecule bound on the capture molecules of the array during the PCR cycles of amplification. To read the presence of the nucleotide target bound on the capture molecules means that the detection has to be performed during one of the steps of the PCR itself, or in a step between the cycles. The reading in a preferred embodiment requires the addition of one and preferably two steps to the cycles, one necessary for the denaturation of the double strands amplicons and the other one for the hybridization itself.

The present invention also covers the machine and apparatus necessary for performing the various steps of the process mainly for diagnostic and/or quantification of a (micro) organism or part of an organism possibly present in a sample that comprises:
 a) capture molecules bound to an insoluble solid support surface at specific locations according to an array;
 b) a device for thermal regulation;
 c) a device for detecting a signal formed at the location of the binding between an amplicon and a capture molecule; and
 d) a computer program for transforming the signal into digital data.

In another embodiment, the computer program further recognizes the locations of the array where a signal is formed.

In a particular embodiment, this apparatus also comprises a reaction chamber for PCR amplification, such that amplification and detection on the array are integrated into the same apparatus in order to detect the hybridized amplicons during the PCR cycles of amplification.

In the apparatus, the capture molecules are preferably single-stranded capture molecules being covalently bound in a location of an array to an insoluble solid support, wherein said capture molecules comprise a capture portion of between 10 and 600 bases, said capture portion being able to specifically bind to said amplicon.

Preferably the array contains at least 2 capture molecules that differ from each other by only one nucleotide.

The apparatus may further comprise a thermal cycler for carrying out an automated PCR amplification of nucleotide sequences obtained from an organism or part of an organism into double-stranded target nucleotide sequences, said thermal cycler being capable of alternately heating and cooling said support for producing labeled target nucleotides.

A preferred apparatus is one in which the detection is performed during the cycles of the amplification.

The device for detecting a signal preferably measures bound target nucleotide sequences on their capture molecules at least 2 times during the PCR, preferably 5 times, more preferably more than 10 times.

In an alternative embodiment the device for detecting a signal measures bound target nucleotide sequences on their capture molecules after the cycles of the amplification are completed.

The apparatus preferably has a detector selected from the method group consisting of: colorimetry, fluorescence, time-resolved fluorescence, photothermal interference contrast, Rayleigh scattering, Raman scattering, surface plasmon resonance, change of mass, quartz crystal microbalances, cantilevers, differential pulse voltametry, chemical cartography by non linear generation frequency spectroscopy, optical change, resistivity, capacitance, anisotropy, refractive index and/or counting nanoparticles.

Preferably the fluorescent scanner uses a laser beam including a confocal scanning method and also preferably a pin hole.

The apparatus may further comprise: a storage system for storing data from different measurements for at least 5 different locations of the support at a defined timing of a thermal cycle; a controller repeating the steps of detection and storage at least one time in at least one thermal cycle for each location of array; and/or a computer program for processing the data obtained in at least one thermal cycle in order to detect and/or quantify the amount of nucleotide molecule present in a sample before amplification.

The apparatus may further comprise:
 a laser source;
 a focusing device for a laser beam produced by said laser source;
 a photomultiplier; and
 a pin hole.

The apparatus may further comprise a computer program for converting a signal formed at a location into data associated with the presence of a particular target.

In a specific embodiment the apparatus is a multifunctional apparatus for amplification and detection of genes, DNA and polynucleotide sequences which performs PCR amplification, polynucleotide detection; real time PCR, quantification real time PCR, Micro-array detection and/or quantification, SNP detection.

The apparatus according to the invention contains two different systems: the first one contains an incubation part in order to obtain the conditions necessary for the amplification and the hybridization of the targets onto their capture molecules. Preferably the first system contains a process for heating so as to provide the temperature for the amplification and the binding reactions to take place. The heating system may be a controlled peltier element, a micro-thin wire heating element laid in a pattern between optical grade polyester sheets like Thermal-Clear™ transparent heaters from Minco, or fluidic system circulating externally temperature regulated fluid. The heating system is composed of an active temperature control system and a temperature control unit (8), allowing to regulate precisely the temperature and to perform temperature cycles. The system also preferably contains a mixing or agitation system for the liquid to be move inside the chamber and increase the reaction rate.

The second system contains the detection system to detect the light emission from the target to be bound to their capture molecules. A light source generates a beam of light to excite the labeled targets on the support. The light source may be a laser that generates a beam having a wavelength of about 532 nm delivered at a power of about 15 mW with a divergence that may be below 1.2 mrad.

The laser beam generated by laser is preferably nearly collimated and nearly Gaussian. An exchangeable excitation filter may be used to collect only the wavelengths of interest. An additional filter wheel may be placed and be used as an attenuation filter to regulate precisely the laser power. This filter wheel may be shaded differently at variable know absorption levels. A lens that may be anti-reflection coated can be used for focusing the laser beam on the support (2). The distance between the light source, the lens and the support may be variable to allow focusing.

Thereafter, the light passes through a dichroic mirror. This mirror may pass light having a wavelength lower than about 530 nm, but reflect light having a wavelength greater than 560 nm. Consequently, the 532 nm light coming from the laser is passed through the dichroic mirror to the support. The light then passes through a chamber (11) and the fluorescent marked sample and reaches the support (2), where bound labeled target are excited and emit fluorescence at about 560 nm. Emitted fluorescence is reflected on the dichroic mirror since its wavelength is greater than about 560 nm to a microscope objective for magnification of the image sample. The fluoresced light is then focused to a photomultiplier tube for detecting the number of photons present therein. In a specific embodiment, an additional emission filter that transmits light having a wavelength greater than about 550 nm may be added. Thus, photomultiplier tube detects substantially only fluoresced light. The Photomultiplier tube generates a pulse for each photon detected. Each of these pulses is amplified and converted to an electronic signal by photoelectric effect. A data acquisition board (7) then collects the resulting signals.

After data are collected from a region of the substrate, the carrier (1) moves support so that light can be directed at a different region on the support (2). The process is repeated until all regions on the substrate have been scanned.

In one embodiment, the solid support containing the capture molecules moves relative to the two systems. The detection of the binding is then performed in the second system independently of the first one.

In another embodiment, the two systems are fixed and work together with no movement of the solid support relative to the two systems.

In still another embodiment, the resolution of the optical system is between 0.1 microns and 500 microns and more preferably between 10 and 100 microns. In another embodiment the distance is different in the incubation system and in the detection system being preferably smaller in the detection system of between 2 and 100 times compared to the incubation system.

Figure 9:
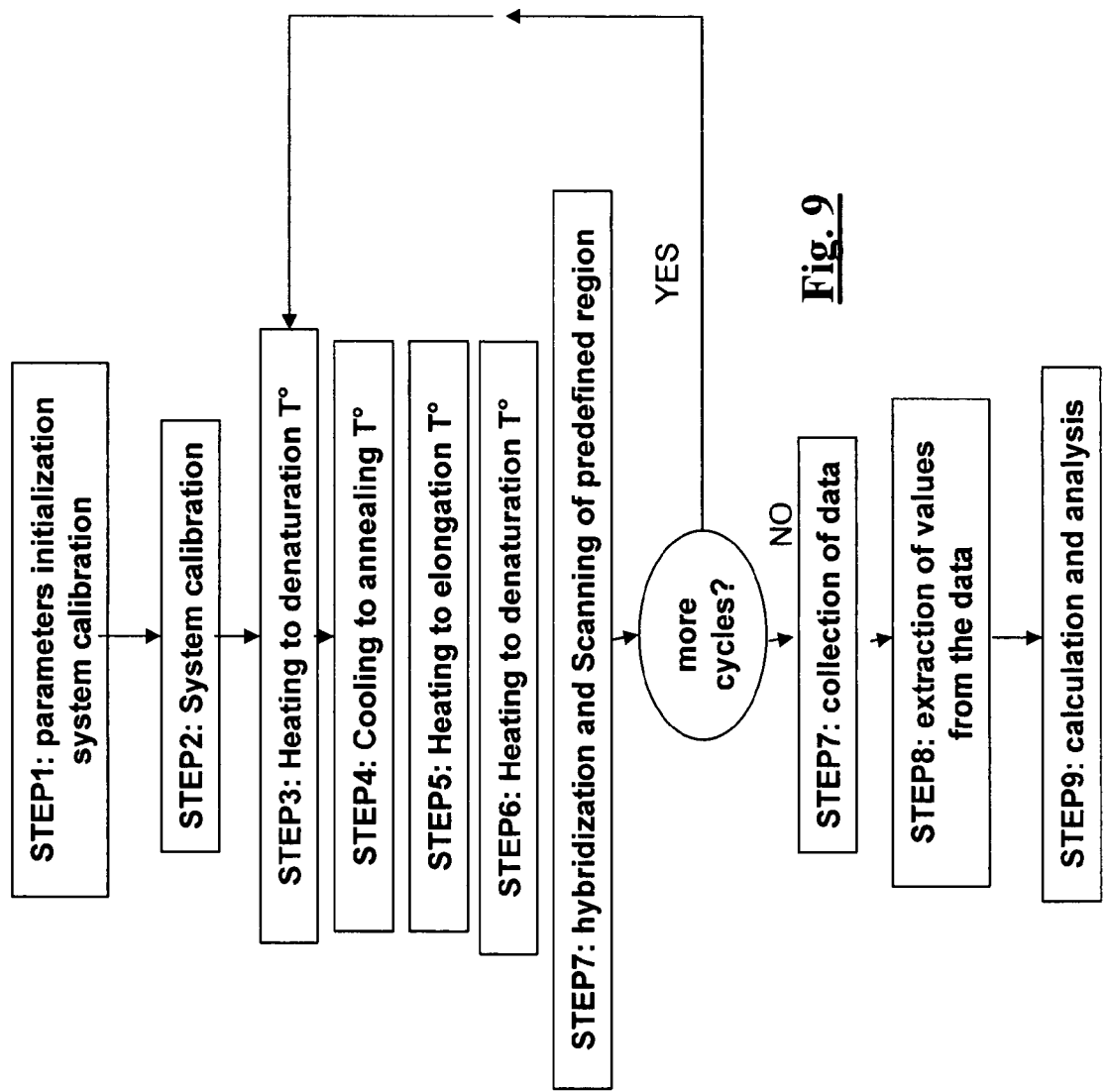
FIG. 9: General schematic flow chart of the different steps of the process according to the invention for making the real time detection together with different cycles of PCR and to stop the detection according to the obtained values. This general flow chart corresponds to the 5 steps cycles of FIG. 7b.

The flowchart of FIG. 9 describes a specific embodiment in which the real-time apparatus is controlled by a programmable computer. The scanner can be a Genepix 4200A scanner from Axon coupled with the scriptable Genepix 6.0 software from Axon.

At STEP 1, the user is prompted to fill in the required parameters, such as: resolution, voltage of the PMT, laser power, scan area, denaturation temperature, denaturation time, annealing temperature, annealing time, elongation temperature, elongation time, and number of cycles.

Explanation of the different parameters.

The resolution defines the pixel size. Generally, a pixel size is chosen that results in more than 50 pixels per synthesis region ("feature"). Setting too high a resolution generates an overload of data while having too low a pixel size generates low quality results.

The PMT voltage multiplies the detected signal. Increasing the laser power will increase the photon count in each pixel.

The "number of cycles" parameter corresponds to the number of times the user wishes to cycle the temperature and scan the substrate. In this manner, the user may perform a series of scans to follow the kinetics of the reactions.

Scan area parameter corresponds to the size of the substrate to be tested. Temperature may vary depending on the type of polymers being tested. Preferably, testing is done at a temperature that produces maximum binding affinity while minimizing mismatches.

The temperature parameters control the temperature of the different amplification steps.

The temperature times parameters defined the duration of each amplification steps. These parameters also define at which moment the detection is performed.

At STEP 2, the system is initialized: the carrier is moved to home position while laser power is checked.

At STEP 3 happens the first heating to the predefined denaturation temperature during the predefined denaturation time.

STEP 4 is similar to STEP 3 for the annealing temperature.

At STEP 5, the first scan is performed and the fluorescence emitted on the selected region of the substrate is collected. The image is saved.

If the number of scans to be done is not reached, then the program performs STEP 6, which is heating to elongation temperature during the predefined duration, and cycles back to STEP 3.

If not, the STEP 7 occurs: the images are gathered for extraction of the signal and background values for each target present on the support.

STEP 8 corresponds to image quantification.

STEP 9 corresponds to data analysis.

The apparatus is able to perform 2 different processes, which have different tasks and require completely different specifications.

The first one is the heating system that has to be perfectly controlled so that the amplifications and hybridizations are performed in conditions where the target polynucleotide can correctly be amplified and bound its capture polynucleotide but not (or non-significantly) homologous or unrelated sequences. Preferably the incubation has to provide a mixing or agitation or movement of the liquid in order to favour the contact between the target molecules, which are in solution with their capture molecules. In a preferred embodiment, the mixing is performed by electrostatic waves or piezoelectric vibrations.

The second one is the detection of target molecules bound to their capture molecules present on the surface of a solid support. The level of detection is on the order of femtomoles or less per spot and this is a challenge to detect the bound targets in the presence of the same molecules in the solution. The scanner has also to perform the detection with the same efficiency on the overall surface otherwise the comparison of the target quantification present in the same sample cannot be done.

The two processes are performed in the integrated system as long as the technical parts (necessary for having the specifications) are compatible with each other. The light source is directed on the surface of the support (2) opposite to the surface in contact with the thermostatized carrier (1).

Detection of other sequences can be advantageously performed on the same array e.g., by allowing an hybridization with a standard nucleotide sequence used for the quantification, with consensus capture molecules for the same or different micro-organisms strains, with a sequence allowing a detection of a possible antibiotic resistance gene by microorganisms or for positive or negative control of hybridization. Said other capture molecules may have a specific sequence longer than 10 to 60 bases and a total length as high as 600 bases and are also bound upon the insoluble solid support, preferably in the array made with the other bound capture molecules related to the invention.

These characteristics described in details for a specific detection and analysis of nucleotide sequences can be adapted by the person skilled in the art for other components of (micro)organisms such as receptors, antibodies, enzymes, etc.

The present invention is further illustrated by the following non-limiting examples.

EXAMPLES

Example 1

Monitoring PCR Amplification of Homologous Sequences on Micro-Array

Capture Molecule Immobilisation

The Diaglass slides (Eppendorf, Hamburg, Germany) were functionalized for the presence of aldehyde according to the method described in patent application WO02/18288. The protocol described in this patent application was followed for the grafting of aminated DNA to aldehyde derivatized glass. The aminated capture molecules were spotted from solutions at concentrations of 3 µM except the BAT-973 which was spotted at 300 nM. The capture molecules were printed onto microscopic glass slides with a home made robotic device using 250 µm diameter pins. The spots were 400 µm in diameter and the volume dispensed was about 0.5 nL. Slides were dried at room temperature and stored at 4° C. until used.

The capture portion of the capture molecules used in this experiment had the following sequences:

```
AATSauG2:
5'-AACTGCTGGACTTATTTTAGGTAAGAG-3'                                  (SEQ ID NO: 3)
AATSpneG2:
5'-CTTGTCATGGGAAATCAGGTATCCA-3'                                    (SEQ ID NO: 4)

BAT-973 (hybridization control):
5' Amine-                                                          (SEQ ID NO: 5)
TAGCCCTCTCACATTTATGAAGCAAGCCCCACTTATTCCCCATTCTTCCTAGTTTTC

TCCTCCCAGGAACTGGGCCAACTCACCTGAGTCACCCTACCTGTGCCTGACCCTAC

TTCTTTTGCTCTTAGCTGTCTGCTCAGACAGAACCCCTACATGAAACAGAAACAAA

AACACTAAAAATAAAAATGGCCATTTGCTTTTTCACCAGATTTGCTAATTTATCCTG

AAATTTCAGATTCCCAGAGCAAAATAATTTTAAACAAAGGTTGAGATGTAAAAGGT

ATTAAATTGATGTTGCTGGACTGTCATAGAAATTACACC-3'

2C9*3:
5'-GGTGGGGAGAAGGTCAAGGTA-3'                                       (SEQ ID NO: 6)

AATSauG1:
5'-TTAATCAATGGTGTACTTAGCTTAAGTA-3'                                 (SEQ ID NO: 7)

AATSpnG1:
5'-TGACCAAAAGGTTTGGAAAACGTGCA-3'                                  (SEQ ID NO: 8)

AATSorG1:
5'-ACTGCCAAGGTTGAAAAGCTCATGG-3'                                   (SEQ ID NO: 9)

AATEfmG1:
5'-TCTGAGGTAGTAGCGGCTATCGATT-3'                                   (SEQ ID NO: 10)

AATEfsG1:
5'-GATTGATGCAACAAGTTTATTGATGGAC-3'                                (SEQ ID NO: 11)
```

At the exception of BAT-973, each capture molecule comprised a spacer portion of 90 bases long at the 5' end of the capture portion, said spacer having the following sequence:

```
5'Amine-                                              (SEQ ID NO: 1)
AAAGTTGAGTCCATTTGTGATGCTAGAAAAGTTGGAACTTTCTTGAACGTCTCCTAT
ATGTCATACATGAATAGGTTGATTTTACTGTAC-3'.
```

DNA Purification

Bacterial strains were grown from single colonies in LB medium (10 g of peptone, 5 g of yeast extract and 5 g of NaCl/1) overnight at 37° C. in aerobic conditions. An aliquot (0.1 ml) of an overnight culture was pelleted by centrifugation (5000 g, 5 min). The bacterial pellet was resuspended in 300 µl of lysis buffer (50 mM Tris HCl pH 8.0, 100 µM EDTA, 150 mM NaCl, 1% SDS) containing 100 µg of lysostaphin (Sigma, Mo., USA) and 100 µg of RNase and incubated at 37° C. for 30 min. Lysis was achieved by incubation at 37° C. for 30 min in the presence of 200 µg of proteinase K (Boehringer, Mannheim, Germany) and boiling for 5 min. Lysate was centrifuged at 4000 g for 5 min and DNA was extracted from 200 µl of supernatant by adsorption on Nucleospin C+T columns (Macherey-Nagel, Düren, Germany), according to the manufacturer's instruction. DNA was eluted in 200 µl of sterile water and stored at −20° C.

PCR and Hybridization

PCR was designed for the amplification of genomic DNA sample from bacteria culture of S. aureus and S. pneumoniae using consensus primers. One positive hybridization control was added to the reaction mixture and corresponded to amplicons labeled with cy3 which were complementary to the capture molecule BAT-973 (SEQ ID NO: 5). This control was used to check the hybridization phase.

The primers used in this experiment have the following sequences:

```
AAPgyr1:
5'- GCNGCDGCRATGCGTTATAC -3'         (SEQ ID NO: 12)

AAPgyr3Cy3:
5'- Cy3- GAACCHYKACCTGTTTCATA -3',   (SEQ ID NO: 13)
``` wherein N=A,G,T, or C; D=G,A, or T; R=A, or G; H=A,T, or C; Y=C, or T; and K=G, or T The amplified product had part of one of its strand sequence specific of capture molecules AATSauG2 (SEQ ID NO: 3) and AATSpneG2 (SEQ ID NO: 4).

A mix of 475 µl for PCR reaction was prepared as follows: 1× concentrated Topo Buffer, dNTP mix (each of dNTP at a final concentration of 200 µM), 0.05 µM of primer AAPgyr1 (SEQ ID NO: 12), 0.1 µM of AAPgyr3Cy3 (SEQ ID NO: 13) Cy3 labeled at 5', Topo Taq DNA polymerase at 5 U in 95 µl, potassium glutamate at 150 mM. 45 µl of this mix was used for each PCR reaction. We added 1 µl genomic DNA extracted from a pure culture of S. aureus (isolated from a clinical sample); 1 µl genomic DNA extracted from a bacterial pure culture of S. pneumoniae (isolated from a clinical sample), 1 µl of distilled water, 2 µl of Cy3-BAT amplicon (40 ng). 50 µl of this PCR reaction was loaded on the micro-array framed by a hybridization chamber, of 9×9 mm sealed with a coverslip in Zeonex having a thickness of 350 µm.

On the backside of the slide, we fixed a special thermocouple which was temperature controlled. The complete heating process test bench was composed of the following relevant components:

"thermocouple": RS-COMPONENT n° 219-4321 Self adhesive thermocouple Type K-Nickel Chromium/Nickel Aluminium (RS components, Northamptonshire, UK), "transmitter": RS-COMPONENT n° 363-0222 Transmitter temperature thermocouple 4-20 mA (RS components, Northamptonshire, UK), "converter": NATIONAL INSTRUMENTS 779026-01 USB-6009 48 Ksamples/sec DAQ multifunction 14 bits for USB (National Instruments, Austin, Tex., USA, "heater": MINCO Heating thermofoil flexible heater: Kapton 0.75"×0.75" HK 5578 R 18,3 L12F (MINCO, Minneapolis, Minn., U.S.A).

The thermocouple, placed as close as possible to the surface to heat, measures the temperature through the transmitter. This temperature information was given to a computer via the converter.

Every second, the software compared the temperature measured to the temperature set point requested by the final user and the controller adjusted the heating in order to provide the requested temperature.

The slide was then entered upside down into the Axon scanner (4100 personal) where it remained during the whole experiment. Scanned was performed with the 532 channel for Cy3 detection at a gain of 600 with a resolution of 20 micrometer.

The heating cover was programmed to make 50 cycles as following: 30 sec at 94° C. (denaturation), 1 min at 56° C. (annealing) and 30 sec at 76° C. (elongation). The fluorescent light emission was determined by scanning the micro-array surface starting 30 sec after the beginning of the annealing step (at 56° C.) of the cycles 5, 10, 15, 19, 20, 25, 30, 33, 35, 37, 39, 41, 43, 45, 47, 48, 49 and 50. The scanner used as excitation light a laser which was focussed on the surface of the support. The emission light was detected and amplified by a photomultiplier. After image acquisition, the scanned 16-bit images were imported to the software, 'Genepix 5" (Axon, Union City, Calif., USA) which was used to quantify the signal intensities. The signal was quantified on two capture molecules AATSauG (SEQ ID NO: 3; S. aureus) and AATSpneG2 (SEQ ID NO: 4; S. pneumoniae) present in three replicates on the array. The local background was subtracted and signal minus background is plotted against the cycle numbers. The arrays also contained capture molecules for negative hybridization control (SEQ ID NOs: 6-11), and positive detection control labeled with Cy3 present in quadruplicate on the array. None of the capture molecule used as negative hybridization control gave positive signals.

Results

Figure 10:
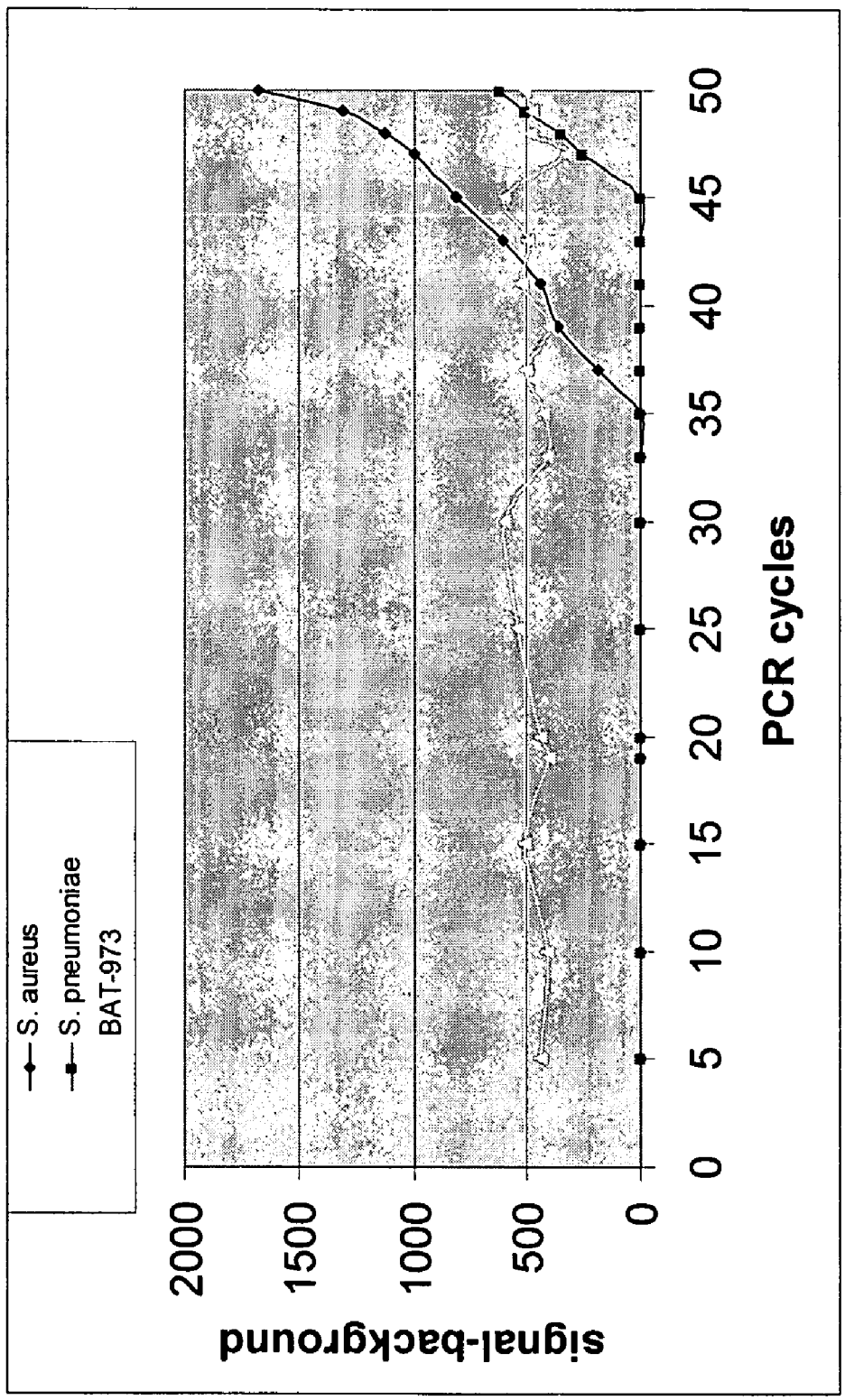
FIG. 10. Results for the online detection of PCR amplification on micro-array using labeled consensus primers provided in Example 1. PCR was performed on genomic DNA of S. aureus and of S. pneumoniae in the presence of a micro-array comprising different bound capture molecules. One capture molecule was specific of the amplified product S. aureus (SEQ ID NO: 3) and another one was specific of the amplified product S. pneumoniae (SEQ ID NO: 4). One positive hybridization control was added to the reaction mixture and corresponded to amplicons labeled with Cy3 which were complementary to the capture molecules BAT-973 (SEQ ID NO: 5). This control was used to check the hybridization phase. Measurements were performed during the annealing step of different thermal cycles on capture molecules of S. aureus (SEQ ID NO: 3), S. pneumoniae (SEQ ID NO: 4) and BAT-973 (SEQ ID NO: 5).

Results of the real-time PCR on micro-array is presented in FIG. 10. The results show the appearance of a signal on the specific capture molecule S. aureus at cycle 37. The signal continues to increase regularly until cycle 50. The signal on capture molecule *S. pneumoniae* starts to appear at cycle 46 and increases regularly until cycle 50. The hybridization control gave a positive signal on its capture molecule BAT-973 (SEQ ID NO: 5) which remained constant with the cycle progression.

Example 2

Monitoring the Kinetics of Hybridization of an Amplicon on a Micro-Array During One Cycle of a 5-Step PCR Process This example corresponds to the embodiment provided in FIG. 7b. The capture molecules sequences and their immobilization were the same as in Example 1 including a spacer. The capture portion of the capture molecule used to follow the hybridization is the following: 2C9*3 (5'-GGTGGG-GAGAAGGTCAAGGTA-3' (SEQ ID NO: 6)).

PCR and Hybridization

The DNA template for the PCR was a plasmidic DNA containing the entire exon 7 of the CYP2C9 gene cloned in vector pCR4 Topo. The plasmid contains a mutation 3. It was amplified by PCR using the following primers.

```
MP2C903:
5'-
Cy3- CTAAAGTCCAGGAAGAGATTGAACG -3'  (SEQ ID NO: 14)

MP2C904:
5'-
CAGAGTGTTGATTTGACAAGATTTTAC -3'    (SEQ ID NO: 15)
```

The expected size of the amplicons was 1114 bp. The amplicon resulting from the amplification was specific of the capture molecule 2C9*3 (SEQ ID NO: 6). The PCR mixture was the following: 1× concentrated Topo Buffer, dNTP mix (each of dNTP at a final concentration of 200 µM), 0.125 µM of primer MP2C903 Cy3 labeled at 5' end (SEQ ID NO: 14), 0.125 µM of MP2C904 (SEQ ID NO: 15), Topo Taq DNA polymerase at 2.5 U in 50 µl, potassium glutamate at 150 mM. We added 5 µl of plasmidic DNA of exon 7 of CYP2C9 carrying the mutation 3 (5 ng/µl) to 45 µl of this PCR mix in a 200 µl PCR tube.

The PCR was performed in a thermocycler (Eppendorf, Hamburg, Germany). Samples were first denatured at 94° C. for 5 min. Then 40 cycles of amplification were performed consisting of 30 sec at 94° C., 1 min at 63° C. and 1 min at 72° C. and a final extension step of 10 min at 72° C.

At the end of the 40 cycles, 50 µl of this PCR reaction was loaded on the micro-array framed by a hybridization chamber and on the backside of the slide, we fixed a special thermocouple as provided in Example 1. The slide was then entered upside down into the Axon scanner (4100 personal). The heating cover was programmed for an additional cycle in 5 steps as following: 30 sec at 94° C. (denaturation) then 5 min at 60° C. (annealing) then 30 sec at 72° C. (elongation) then 30 sec at 94° C. (denaturation) and finally 5 min at 40° C. (hybridization).

During this cycle of 5 temperatures, the array was scanned at different time points (corresponding to the capture molecule 2C9*3 scanning time) of 0 sec, 80 sec, 140 sec, 220 sec, 300 sec, 380 sec, 450 sec, 530 sec, 600 sec, 680 sec, 760 sec and 840 sec.

Scanning was performed as in Example 1 except that a gain of 500 was used instead of 600. The signal was quantified on capture molecule MT2C9*3 (SEQ ID NO: 6) present in three replicates on the array. The local background was subtracted and signal minus background is plotted against the time of the 5 steps of the cycle 41.

Results

Figure 11:
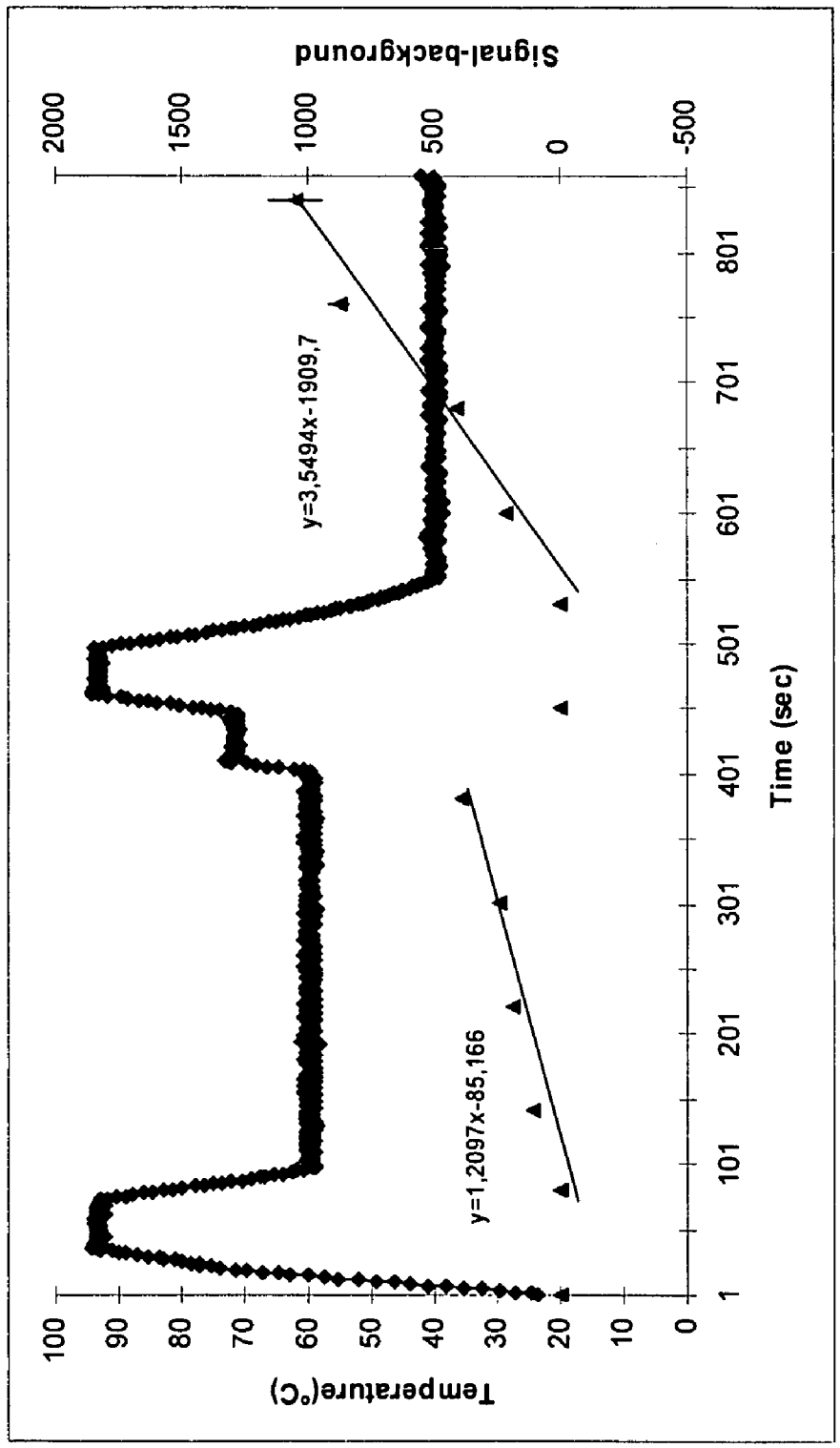
FIG. 11 shows the results of monitoring the kinetics of hybridization of an amplicon on a micro-array during one cycle of the amplification/detection in 5 steps as provided in FIG. 7b. PCR was performed on the CYP2C9 gene in the presence of a micro-array comprising different bound capture molecules. One capture molecule was specific of the amplified product MT2C9*3 (SEQ ID NO: 6). Measurements were performed regularly during the 5 steps of cycle 41: denaturation at 94° C., annealing at 60° C. elongation at 72° C. denaturation at 94° C. and hybridization at 40° C. T° C. (♦). Regression curves of the signal increase during the steps of annealing and hybridization were provided (▲).

Results are presented in FIG. 11. The results show a signal on the specific capture molecule MT2C9*3 (SEQ ID NO: 6). The signal appeared during the annealing step at 60° C. The signal increased regularly until the end of the annealing step. Then the signal was lost during the steps of elongation and denaturation and came back to the background level. Then the signal appeared again during the hybridization step at 40° C. and increased regularly until the end of the hybridization step. The regression curves of the signal increase during the steps of annealing and hybridization are provided in FIG. 11.

Example 3

Monitoring the Kinetics of Hybridization of an Amplicon on a Micro-Array During Three Cycles of a 5 Steps PCR Process This example corresponds to the embodiment provided in FIG. 7b.

The capture molecules sequences and their immobilization were the same as in Example 1 including a spacer. The experiment was performed as provided in Example 2, except for the following: we added 10 µl of plasmidic DNA of exon 7 of CYP2C9 carrying the mutation 3 (5 ng/µl) to 90 µl of PCR mix in a 200 µl PCR tube.

The PCR was performed in a thermocycler (Eppendorf, Hamburg, Germany). Samples were first denatured at 94° C. for 5 min. Then 40 cycles of amplification were performed consisting of 30 sec at 94° C., 1 min at 63° C. and 1 min at 72° C., then a final step at 72° C. for 10 min.

After PCR cycles 25, 30 and 35, 30 µl of the PCR product was taken from the PCR tube and was loaded on the micro-array framed by a hybridization chamber. On the backside of the slide we fixed a special thermocouple as provided in Example 1. The slide was then entered upside down into the Axon scanner (4100 personal).

The heating cover was programmed for an additional cycle in 5 steps as follows: 30 sec at 94° C. (denaturation) then 1 min at 63° C. (annealing) then 30 sec at 72° C. (elongation) then 30 sec at 94° C. (denaturation) and finally 5 min at 55° C. (hybridization). During this cycle of 5 temperatures, the array was scanned at different time points (corresponding to the capture molecule 2C9*3 scanning time) of 0 sec, 100 sec, 300 sec, 400 sec, 500 sec and 600 sec. The reading was repeated for PCR product taken after cycles 30 and 35.

Scanning was performed as in Example 1 except that a gain of 550 was used instead of 600. The signal was quantified on capture molecule MT2C9*3 (SEQ ID NO: 6) present in three replicates on the array. The local background was subtracted and signal minus background is plotted against the time of the 5 steps of cycles 26, 31, and 36.

Results

Figure 12:
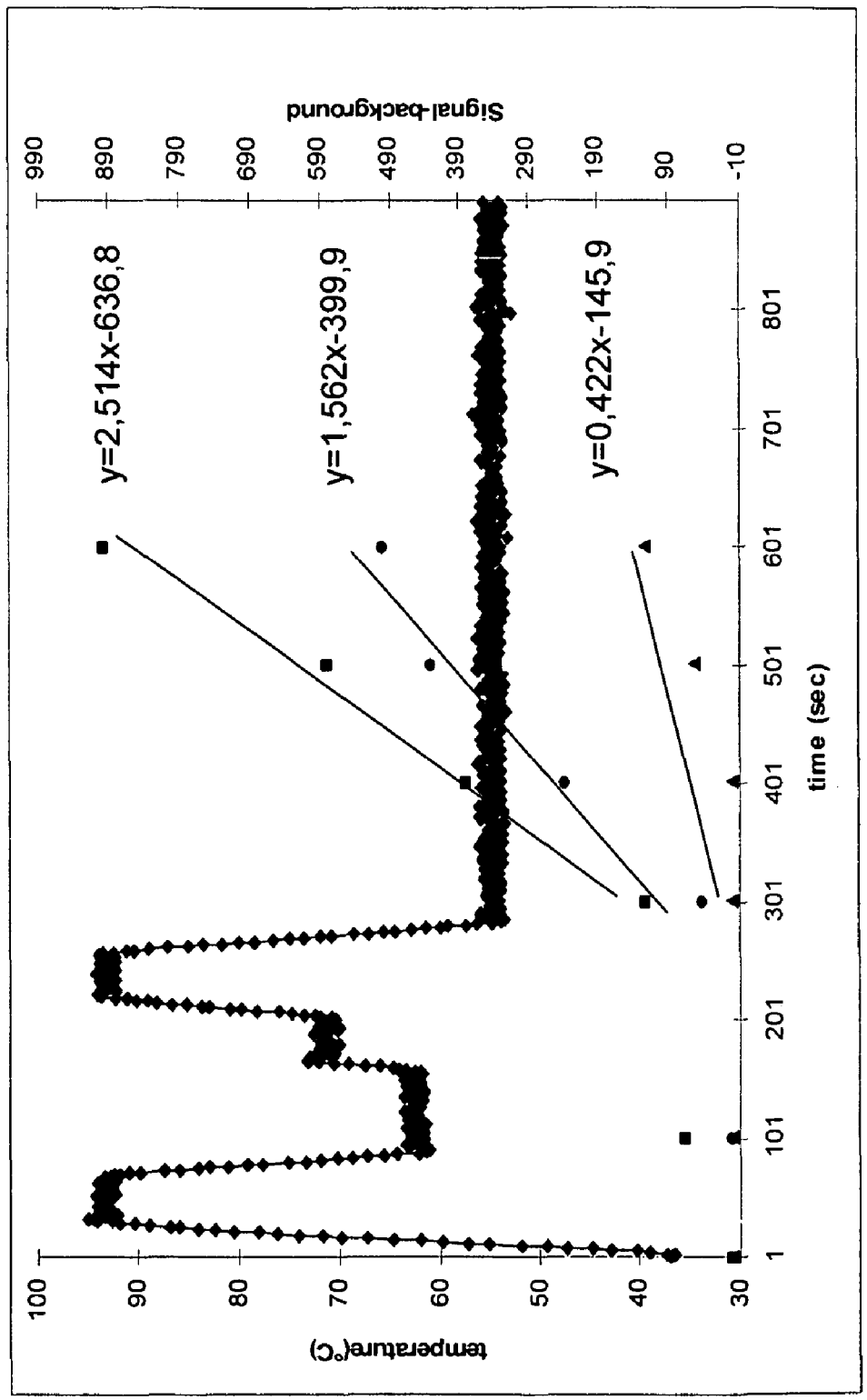
FIG. 12 shows the results of monitoring the kinetics of hybridization of an amplicon on a micro-array during three cycles of the amplification/detection in 5 steps. The experiment was conducted as provided in FIG. 11. Measurements were performed at regular intervals during the hybridization step at cycles 26 (▲), 31 (●), and 36 (■) and regression curves related to these measurements were provided. T° C. (♦).

Results are presented in FIG. 12. One measurement was effected during the annealing step (at time point of 100 sec). Signals were very low for the three measured cycles and were in the range of the background level. The next fours measurements (a time points of 300 sec, 400 sec, 500 sec and 600 sec) were made during the hybridization step. Signals were observed on the specific capture molecule MT2C9*3 (SEQ ID NO: 6). The signals increase linearly with time of hybridization and the slopes of the curves increase with the cycle number (slope=0.422 for cycle $26^{th}$, 1.562 for cycle 31 and 2.514 for cycle 36). The regression curves of the time frame of the signal during the hybridization step are provided in FIG. 12.

Example 4

Monitoring the Kinetics of Hybridization of an Amplicon on a Micro-Array During Multiple Cycles of a 5 Steps PCR Process The capture molecules sequences and their immobilization were the same as in Example 1 including a spacer. The experiment was performed as provided in Example 3, except for the following aspect: 50 μl of this PCR reaction was loaded on the micro-array framed by a hybridization chamber as provided in Example 1.

The temperature of the PCR was controlled by the thermocouple fixed on the backside of the slide as in Example 1. The slide was then entered upside down into the Axon scanner (4100 personal) where it remained during the whole experiment.

The heating cover was programmed to first denature the sample for 5 min at 94° C. Then 50 cycles of amplification were performed in a 5 steps PCR consisting of: 30 sec at 94° C. (denaturation) then 1 min at 63° C. (annealing) then 30 sec at 72° C. (elongation) then 30 sec at 94° C. (denaturation) and finally 5 min at 55° C. (hybridization).

Scanning was performed as in Example 3. During the PCR cycles 35, 40 and 45, the array was scanned at different time points after the beginning of the cycle (corresponding to the capture molecule 2C9*3 scanning time): 0 sec, 100 sec, 300 sec, 400 sec, 500 sec and 600 sec.

Signals were observed on the specific capture molecule MT2C9*3 (SEQ ID NO: 6). The signals increase linearly with time of hybridization and the slopes of the curves increase with the cycle number.

The invention has been described by reference to certain embodiments discussed above. It will be recognized that these embodiments are susceptible to various modifications and alternative forms well known to those of skill in the art. Many modifications in addition to those described above may be made to the structures and techniques described herein without departing from the spirit and scope of the invention. Accordingly, although specific embodiments have been described, these are examples only and are not limiting upon the scope of the invention.

All publications, sequences of accession numbers, and patent applications cited in this specification are herein incorporated by reference as if each individual publication or patent application were specifically and individually indicated to be incorporated by reference.

What is claimed is:

1. A diagnostic and/or quantification kit of a biological organism or part of an organism comprising:
   (a) specific primers for the amplification of a nucleotide sequence;
   (b) a fluorescent label for labelling the amplified sequence;
   (c) an insoluble solid support surface upon which single-stranded unlabeled capture molecules are covalently bound, said capture molecules being disposed upon the surface of the solid support according to an array, wherein said capture molecules comprise a spacer portion comprising a nucleotide sequence of at least 40 bases in length and a capture portion of between 10 and 60 bases which is able to specifically bind to a nucleotide sequence of said organism or part of it; and
   (d) a closed reaction chamber for performing a genetic amplification together with the identification and/or quantification of amplified nucleotide sequences from said organism or part of it.

2. The diagnostic and/or quantification kit of claim 1, wherein the capture portion of the capture molecules contain from 15 to 40 nucleotides able to specifically bind to the nucleotide sequence of said organism or part of it.

3. The diagnostic and/or quantification kit of claim 1, wherein the capture portion of the capture molecules contain from 20 to 30 nucleotides able to specifically bind to the nucleotide sequence of said organism or part of it.

4. The diagnostic and/or quantification kit of claim 1, wherein the capture molecules are immobilized by a 5' end.

5. The diagnostic and/or quantification kit of claim 1, wherein the capture molecules are immobilized by a 3' end.

6. The diagnostic and/or quantification kit of claim 1, wherein the array comprises at least 4 different capture molecules that bind specifically to at least 4 homologous amplified nucleotide sequences of the organisms or part of it.

7. The diagnostic and/or quantification kit of claim 6, wherein the density of the array is at least 4 different capture molecules per cm$^2$ of solid support surface.

8. The diagnostic and/or quantification kit of claim 1, wherein the capture molecules are immobilized on a solid support such that the spacer portion is located between the solid support and the capture portion.

9. The diagnostic and/or quantification kit of claim 1, wherein the spacer portion is a polynucleotide chain having a length of at least 90 nucleotides.

10. The diagnostic and/or quantification kit of claim 1, wherein the spacer portion has at least 60% homology with SEQ ID NO: 2.

11. The diagnostic and/or quantification kit of claim 1, wherein the spacer portion has at least 60% homology with SEQ ID NO: 3.

12. The diagnostic and/or quantification kit of claim 1, wherein the kit further comprises one or more of the following: a dNTP, a thermostable DNA polymerase, a buffer, and a nucleotide molecule to be used as an internal standard.

13. The diagnostic and/or quantification kit of claim 1, wherein the material for the support is selected from the group consisting of glass, an electronic device, a silicon support, a plastic support, a compact disc, a gel layer, silica, metal and mixtures thereof.

14. A diagnostic and/or quantification kit of a biological organism or part of an organism comprising:
   (a) specific primers for the amplification of a nucleotide sequence;
   (b) a fluorescent label for labelling the amplified sequence;
   (c) an insoluble solid support surface upon which single-stranded unlabeled capture molecules are covalently bound, said capture molecules being disposed upon the surface of the solid support according to an array, wherein said capture molecules comprise a spacer portion comprising a nucleotide sequence of at least 40 bases in length and a capture portion of between 10 to 60 bases which is able to specifically bind to a nucleotide sequence of said organism or part of it;
   (d) a closed reaction chamber for performing a genetic amplification together with the identification and/or quantification of amplified nucleotide sequences from said organism or part of it; and
   (e) a microlaboratory system based upon the use of microfluidic technology which is able to perform the genetic amplification and the identification of amplified nucleotide sequence upon the same solid support.

* * * * *